(12) United States Patent
Chu et al.

(10) Patent No.: US 6,716,840 B2
(45) Date of Patent: Apr. 6, 2004

(54) GUANIDINO COMPOUNDS

(75) Inventors: Daniel Chu, Santa Clara, CA (US); Rustum S. Boyce, San Francisco, CA (US); David Duhl, Oakland, CA (US); Bryan H. Chang, Concord, CA (US)

(73) Assignee: Chiron Corporation, Emeryville, CA (US)

( * ) Notice: Subject to any disclaimer, the term of this patent is extended or adjusted under 35 U.S.C. 154(b) by 0 days.

(21) Appl. No.: 10/118,730

(22) Filed: Apr. 8, 2002

(65) Prior Publication Data

US 2002/0193595 A1 Dec. 19, 2002

Related U.S. Application Data

(60) Provisional application No. 60/282,847, filed on Apr. 9, 2001.

(51) Int. Cl.$^7$ .................... A61K 31/5375; C07D 413/12

(52) U.S. Cl. .................... 514/233.5; 544/144; 544/373; 546/201; 548/465; 514/254.01

(58) Field of Search .................... 514/233.5, 254.01; 544/144, 373; 546/201; 548/465

(56) References Cited

U.S. PATENT DOCUMENTS

| | | |
|---|---|---|
| 4,732,916 A | 3/1988 | Satoh et al. |
| 4,824,835 A | 4/1989 | Mertens et al. ............. 514/278 |
| 4,874,864 A | 10/1989 | Schnur et al. |
| 4,948,891 A | 8/1990 | Schnur et al. |
| 4,948,901 A | 8/1990 | Schnur et al. |
| 5,086,057 A | 2/1992 | Sasagawa |
| 5,124,328 A | 6/1992 | Fisher et al. |
| 5,352,704 A | 10/1994 | Okuyama et al. |
| 5,362,902 A | 11/1994 | Barnish et al. |
| 5,547,966 A | 8/1996 | Atwal et al. |
| 5,637,439 A | 6/1997 | Kaneko et al. |
| 5,731,408 A | 3/1998 | Hadley et al. |
| 5,750,573 A | 5/1998 | Bianchi et al. |
| 5,885,985 A | 3/1999 | Macdonald et al. |
| 5,889,025 A | 3/1999 | Lohray et al. |
| 5,952,381 A | 9/1999 | Chen et al. |
| 5,962,530 A | 10/1999 | Engel et al. |
| 6,020,349 A | 2/2000 | Ankersen et al. |
| 6,030,985 A | 2/2000 | Gentile et al. |
| 6,054,556 A | 4/2000 | Huby et al. |
| 6,060,589 A | 5/2000 | Stark et al. |
| 6,127,343 A | 10/2000 | Ankersen et al. |

FOREIGN PATENT DOCUMENTS

| | | |
|---|---|---|
| EP | 0343894 | 11/1989 |
| EP | 354553 | 2/1990 |
| WO | WO 96/04270 | 2/1996 |
| WO | WO 96/24580 | 8/1996 |
| WO | WO 97/19911 | 6/1997 |
| WO | WO 97/41119 | 11/1997 |
| WO | WO 98/07420 | 2/1998 |
| WO | WO 99/64002 | 12/1999 |
| WO | WO 00/17191 | 3/2000 |
| WO | WO 00/74679 | 12/2000 |
| WO | WO 01/10842 | 2/2001 |
| WO | WO 01/55106 | 8/2001 |
| WO | WO 01/55107 | 8/2001 |
| WO | WO 01/55109 | 8/2001 |
| WO | WO 01/70337 | 9/2001 |
| WO | WO 01/70708 | 9/2001 |

OTHER PUBLICATIONS

Kathleen G. Mountjoy et al.: "The Cloning of a Family of Genes that Encode the Melanocortin Receptors," Science, 1992, vol. 257, pp. 1248–125.

Dennis Huszar et al.: "Targeted Disruption of the Melanocortin–4 Receptor Results in Obesity in Mice," Cell, 1997, vol. 88, pp. 131–141, Cell Press.

M.E. Hadley et al.: The Proopiomelanocortin System, Annals New York Academy of Sciences, pp. 1–21.

L.L. Kiefer et al: "Mutations in the Carboxyl Terminus of the Agouti Protein Decrease Agouti Inhibition of Ligand Binding to the Melanocortin Receptors," Biochemistry, 1997, 36, pp. 2084–2090, American Chemical Society.

(List continued on next page.)

Primary Examiner—Joseph K. McKane
Assistant Examiner—Golam M M Shameem
(74) Attorney, Agent, or Firm—Steven W. Collier; Bernard P. Friedrichsen; Robert P. Blackbur

(57) ABSTRACT

Compounds having the general structure I are provided:

$$R^1L-N\underset{Y}{\overset{X}{\diagdown}}\underset{Z^3}{\overset{Z^1}{\diagdown}}\underset{Z^2}{\overset{W}{\diagup}} \quad I$$

X and Y are independently selected from the group consisting of $CH_2$, N, $NR^9$, C=O, C=S, S=O, $SO_2$, S, O, $(CR^6R^7)_n$, $C(=O)-(CR^6R^7)_n$, and $C(=S)-(CR^6R^7)_n$, where n is 1, 2, or 3. W is selected from the group consisting of

[two guanidino structures shown with substituents $R^2$, $R^3$, $R^4$, $R^5$] and ;

and L is selected from the group consisting of N, O, S, S=O, $SO_2$, C(O), NC(O), NC(S), OC(O), OC(S), $C(NR^{10})$, $C(NOR^{10})$, and a covalent bond. $Z^1$, $Z^2$, and $Z^3$ are independently selected from the group consisting of substituted carbon and nitrogen. Compounds of formula I are agonists of the melanocortin-4 receptor ("MC-4r") and therefore may have useful properties for controlling diseases related to MC-4r action in humans, such as obesity and type II diabetes.

20 Claims, No Drawings

OTHER PUBLICATIONS

Dongsi Lu et al:, "Agouti Protein is an Antagonist of the Melanocyte–Stimulating–Hormone Receptor," Nature, 1994, vol. 371, pp. 799–802.

T.M. Fong et al.: "ART (Protein Product of Agouti–Related Transcript as an Antagonist of MC–3 and MC–4 Receptors," Biochemical and Biophysical Research Communications, 1997, 237, pp. 629–631, Academic Press.

M. Rossi et al.: "A C–Terminal Fragment of Agouti–Related Protein Increases Feeding and Antagonizes the Effect of Alpha–Melanocyte Stimulating Hormone in Vivo," Endocrinology, 1998, vol. 139, No. 10, pp. 4428–4431.

Jerry March: Advanced Organic Chemistry—Reactions, Mechanisms and Structure, 1985, John Wiley & Sons.

Francis A. Carey et al.: Advanced Organic Chemistry A and B $3^{rd}$ ed., 1990, Plenium Press, New York.

Brian S. Furniss et al.: Vogel's Textbook of Practical Organic Chemistry $5^{th}$ ed., 1989, Longman Scientific & Technical & John Wiley & Sons, Inc., New York.

Theodora W. Greene: Protective Groups in Organic Synthesis $1^{st}$ ed., 1981, John Wiley & Sons, New York, NY.

Richard C. Larock: Comprehensive Organic Transformations—A Guide to Functional Group Preparations, 1989, VCH Publisher's Inc., New York.

Ian Bell et al.: "Efficient Synthesis of 1–Heterocyclic–3–Aminopyrrolidinones," Tetrahedron Letters, 2000, pp. 1141–1145, Elsevier Science, Ltd.

XP–001064218, Marc Julia et al.: "Amidines et Guanidines Apparentées à la Congocidine," Bulletin De La Société Chemique de France, 1968, No. 1, pp. 376–382.

James J. Sims et al.: "6–Methoxy–β–Tetralone," Organic Synthesis, pp. 109–113.

David M. Tschaen et al.: "Asymmetric Synthesis of MK–0499," J. Org. Chem., 1995, 60, pp. 4324–4330, American Chemical Society.

John B. Nevy et al. "Transition State Imbalance in the Deprotonation of Substituted 2–Tetralones by Hydroxide Ion," J. Am. Chem. Soc., 1997, 119, pp. 12722–12726, American Chemical Society.

Dominick A. Quagliato et al.: "Efficient Procedure for the Reduction of α–Methylamines," J. Org. Chem., 2000, 65, pp. 5037–5042, American Chemical Society.

John W. Mickelson et al.: "Asymmetric Synthesis of 2,6–Methylated Piperazines," J. Org. Chem., 1995, 60, pp. 4177–4183, American Chemical Society.

H.C. Brown et al.: "Organoboranes for Synthesis. 7. An Improved General Synthesis of Primary Amines From Alkenes via Hydroboration–Organoborane Chemistry," Tetrahedron, 1987, vol. 43, No. 18, pp. 4071–4078, Pergamon Journals Ltd.

Sukanta Bhattacharyya et al.: "Selective Monoalkylation of Ammonia: A High Throughput Synthesis of Primary Amines," Synlett, 1999, No. 11, pp. 1781–1783, Thieme Stuttgart, New York.

Jose Alexander et al.: "(Acyloxy)alkyl Carbamates as Novel Bioreversible Prodrugs for Amines: Increased Permeation through Biological Membranes," J. Med. Chem., 1988, 31, pp. 318–322, American Chemical Society.

Joseph Weinstock et al.: "Synthesis and Evaluation of Non–Catechol D–1 and D–2 Dopamine Receptor Agonists: Benzimidazol–2–one, Benzoxazol–2–one, and the Highly Potent Benzothiazol–2–one 7–Ethylamines," J. Med. Chem., 1987, 30, pp. 1166–1176, American Chemical Society.

Website: http://www.idealibrary.com/links/doi/10.1006/bbrc.1997., Abstract—Tung Ming Fong et al.: "ART (Protein Product of Agouti–Related Transcript) as an Antagonist of MC–3 and MC–4 Receptors," Biochemical and Biophysical Research Communications, 1997, vol. 237, No. 3.

Website: wysiwyg://36/http://www.sciencemag.org/. . . ar=2001&hits=10&sendit.x=36&sendit.y, Michael M. Ollmann et al.: "Antagonism of Central Melanocortin Receptors in Vitro and in Vivo by Agouti–Related Protein," Science, 1997, 278, pp. 135–138.

Michael M. Ollmann et al.: "Antagonism of Central Melanocortin Receptors in Vitro and in Vivo by Agouti–Related Protein," Science, 1997, vol. 278, pp. 135–138.

GUANIDINO COMPOUNDS

CROSS-REFERENCES TO RELATED APPLICATIONS

This application claims priority to U.S. Provisional Application No. 60/282,847 filed Apr. 9, 2001, the entire disclosure of which is incorporated herein by reference and for all purposes.

FIELD OF THE INVENTION

This invention relates to melanocortin-4 receptor (MC4-R) agonists and methods of their preparation. The invention also relates to methods of treating melanocortin-4 receptor-mediated diseases, such as obesity or diabetes, by activating the melanocortin-4 receptor with compounds provided herein.

BACKGROUND OF THE INVENTION

Melanocortins are peptide products resulting from post-translational processing of pro-opiomelanocortin and are known to have a broad array of physiological activities. The natural melanocortins include the different types of melanocyte stimulating hormone (α-MSH, β-MSH, γ-MSH) and ACTH. Of these, α-MSH and ACTH are considered to be the main endogenous melanocortins.

The melanocortins mediate their effects through melanocortin receptors (MC-R), a subfamily of G-protein coupled receptors. There are at least five different receptor subtypes (MC1-R to MC5-R). MC1-R mediates pigmentation of the hair and skin. MC2-R mediates the effects of ACTH on steroidogenisis in the adrenal gland. MC3-R and MC4-R are predominantly expressed in the brain. MC5-R is considered to have a role in the exocrine gland system.

The melanocortin-4 receptor (MC4-R) is a seven-transmembrane receptor. MC4-R may participate in modulating the flow of visual and sensory information, coordinate aspects of somatomotor control, and/or participate in the modulation of autonomic outflow to the heart. *Science* 1992 257:1248–125. Significantly, inactivation of this receptor by gene targeting has resulted in mice that develop a maturity onset obesity syndrome associated with hyperphagia, hyperinsulinemia, and hyperglycemia. *Cell* Jan. 10, 1997; 88(1): 131–41. MC4-R has also been implicated in other disease states including erectile disorders, cardiovascular disorders, neuronal injuries or disorders, inflammation, fever, cognitive disorders, and sexual behavior disorders. Hadley M. E. and Haskell-Luevano C., The proopiomelanocortin system. *Ann N Y Acad Sci*, Oct. 20, 1999; 885:1.

Furthermore, observations in connection with endogenous MCx-R antagonists indicate that MC4-R is implicated in endogenous energy regulation. For example, an agouti protein is normally expressed in the skin and is an antagonist of the cutaneous MC receptor involved in pigmentation, MC1-R. M. M. Ollmann et al., *Science*, 278:135–138 (1997). However, overexpression of agouti protein in mice leads to a yellow coat color due to antagonism of MC1-R and increased food intake and body weight due to antagonism of MC4-R. L. L. Kiefer et al., *Biochemistry*, 36: 2084–2090 (1997); D. S. Lu et al., *Nature*, 371:799–802 (1994). Agouti related protein (AGRP), an agouti protein homologue, antagonizes MC4-R but not MC1-R. T. M. Fong et al., *Biochem. Biophys. Res. Commun.* 237:629–631 (1997). Administration of AGRP in mice increases food intake and causes obesity but does not alter pigmentation. M. Rossi et al., *Endocrinology*, 139:4428–4431 (1998).

Together, this research indicates that MC4-R participates in energy regulation, and therefore, identifies this receptor as a target for a rational drug design for the treatment of obesity.

In connection with MC4-R and its uncovered role in the etiology of obesity and food intake, the prior art has reported compounds or compositions that act as agonists or antagonists of MC4-R. As examples, U.S. Pat. No. 6,060,589 describes polypeptides that are capable of modulating signaling activity of melanocortin receptors. Also, U.S. Pat. Nos. 6,054,556 and 5,731,408 describe families of agonists and antagonists for MC4-R receptors that are lactam heptapeptides having a cyclic structure.

There is a need to for potent and specific agonists of MC4-R that are low molecular weight non-peptide small molecules. Methods of treating a melanocortin-4 receptor mediated disease, such as obesity, with such non-peptide drugs, are also particularly desirable.

SUMMARY OF THE INVENTION

The instant invention provides potent and specific agonists of MC4-R that are low molecular weight non-peptide small molecules. Thus, there has been provided, in accordance with one aspect of the invention, a compound of formula I:

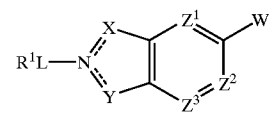

wherein

X and Y are independently selected from the group consisting of $CH_2$, N, $NR^9$, C=O, C=S, S=O, $SO_2$, S, O, $(CR^6R^7)_n$, C(=O)—$(CR^6R^7)_n$; and C(=S)—$(CR^6R^7)_n$;

n is 1, 2, or 3;

W is selected from the group consisting of

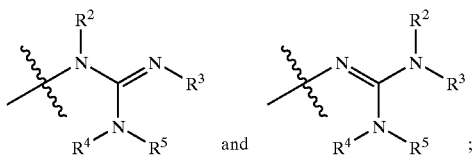

L is selected from the group consisting of N, O, S, S=O, $SO_2$, C(O), NC(O), NC(S), OC(O), OC(S), $C(NR^{10})$, $C(NOR^{10})$, and a covalent bond;

$Z^1$, $Z^2$, and $Z^3$ are independently selected from the group consisting of $CR^8$ and N;

$R^1$ is selected from the group consisting of H, and substituted and unsubstituted arylalkyl, heteroarylalkyl, aryl, heteroaryl, heterocyclyl, cycloalkyl, heterocyclylalkyl, cycloalkylalkyl, alkenyl, alkynyl, and alkyl groups;

$R^2$ is selected from the group consisting of H, and substituted and unsubstituted alkyl, alkenyl, alkynyl, cycloalkylalkyl, aryl, and arylalkyl groups;

$R^3$ is selected from the group consisting of H, and substituted and unsubstituted alkyl, alkenyl, alkynyl, cycloalkyl, heteroaryl, heterocyclyl, heterocyclylalkyl, arylalkyl, heteroarylalkyl, and cycloalkylalkyl groups, or $R^2$ and $R^3$ may join together to form a ring containing at least two N atoms;

R⁴ is selected from the group consisting of H, and substituted and unsubstituted alkyl, alkenyl, alkynyl, cycloalkyl, aryl, heteroaryl, heterocyclyl, arylalkyl, heteroarylalkyl, and cycloalkylalkyl groups, or $R^2$ and $R^4$ may join together to form a ring containing at least two N atoms;

R⁵ is selected from the group consisting of H, and substituted and unsubstituted alkyl, alkenyl, alkynyl, cycloalkyl, aryl, heteroaryl, heterocyclyl, arylalkyl, heteroarylalkyl, and cycloalkylalkyl groups, or $R^4$ and $R^5$, together with the nitrogen to which they are bound, form a substituted or unsubstituted heterocyclyl or heteroaryl group, or $R^3$ and $R^5$ may join together to form a ring containing at least two N atoms;

R⁶ and R⁷ may be the same or different, and are each independently selected from the group consisting of H, Cl, I, F, Br, OH, $NH_2$, CN, $NO_2$, and substituted and unsubstituted alkoxy, amino, alkyl, alkenyl, alkynyl, alkylamino, dialkylamino, cycloalkyl, heterocyclylamino, heteroarylamino, aminocarbonyl, alkylaminocarbonyl, dialkylaminocarbonyl, cycloalkylaminocarbonyl, arylaminocarbonyl, heterocyclylaminocarbonyl, and heteroarylaminocarbonyl groups;

R⁸ is independently selected from the group consisting of H, Cl, I, F, Br, OH, $NH_2$, CN, $NO_2$, and substituted and unsubstituted alkoxy, amino, alkyl, alkenyl, alkynyl, alkylamino, dialkylamino, cycloalkyl, heterocyclylamino, heteroarylamino, aminocarbonyl, alkylaminocarbonyl, dialkylaminocarbonyl, cycloalkylaminocarbonyl, arylaminocarbonyl, heterocyclylaminocarbonyl, and heteroarylaminocarbonyl groups; and R⁹ and R¹⁰ are independently selected from the group consisting of H, and substituted and unsubstituted alkyl, alkenyl, alkynyl, cycloalkyl, aryl, heteroaryl, heterocyclyl, arylalkyl, heteroarylalkyl, cycloalkylalkyl, alkylcarbonyl, and arylcarbonyl groups.

Compounds provided by the invention further include prodrugs of the compound of formula I, pharmaceutically acceptable salts thereof, stereoisomers thereof, tautomers thereof, hydrates thereof, hydrides thereof, or solvates thereof.

In one embodiment, X is $CH_2$ and Y is C=O.

In another embodiment, X is C=O and Y is $CH_2$.

In another embodiment, X is C=O and Y is C=O.

In other embodiments, L is a covalent bond, and X and Y have the values according to any of the previous embodiments.

In another embodiment, $Z^1$, $Z^2$, and $Z^3$ are all CH, and X, Y, and L have the values according to any of the previous embodiments.

In another embodiment, at least one of $Z^1$, $Z^2$, or $Z^3$ is N, and X, Y, and L have the values according to any of the previous embodiments.

In another embodiment, X, Y, L, $Z^1$, $Z^2$, and $Z^3$ have any of the values of previous embodiments, and $R^1$ is selected from the group consisting of substituted and unsubstituted arylalkyl, alkenyl, heteroarylalkyl, and heterocyclylalkyl groups.

In another embodiment, X, Y, L, $Z^1$, $Z^2$, and $Z^3$ have any of the values of previous embodiments, and $R^1$ is 2,4-disubstituted phenethyl.

In another embodiment, X, Y, L, $Z^1$, $Z^2$, and $Z^3$ have any of the values of previous embodiments, and $R^1$ is selected from the group consisting of 2,4-dihalophenethyl, and 2,4-dialkylphenethyl.

In another embodiment, X, Y, L, $Z^1$, $Z^2$, and $Z^3$ have any of the values of previous embodiments, and $R^1$ is selected from the group consisting of phenethyl, 2,4-dichlorophenethyl, 4-methoxyphenethyl, 4-bromophenethyl, 4-methylphenethyl, 4-chlorophenethyl, 4-chlorobenzyl, 4-ethylphenethyl, cyclohexenylethyl, 2-methoxyphenethyl, 2-chlorophenethyl, 2-fluorophenethyl, 3-methoxyphenethyl, 3-fluorophenethyl, thienylethyl, indolylethyl, 4-hydroxyphenethyl, and 3,4-dimethoxyphenethyl.

In another embodiment, X, Y, L, $Z^1$, $Z^2$, $Z^3$, and $R^1$ have any of the values of previous embodiments, and $R^2$ is H.

In another embodiment, X, Y, L, $Z^1$, $Z^2$, $Z^3$, $R^1$, and $R^2$ have any of the values of previous embodiments, and $R^3$ is selected from the group consisting of substituted and unsubstituted alkyl, alkenyl, alkynyl, cycloalkyl, heteroaryl, heterocyclyl, heterocyclylalkyl, arylalkyl, heteroarylalkyl, and cycloalkylalkyl groups.

In another embodiment, X, Y, L, $Z^1$, $Z^2$, $Z^3$, $R^1$, and $R^2$ have any of the values of previous embodiments, and $R^3$ is selected from the group consisting of substituted and unsubstituted cycloalkyl, alkenyl, alkyl, and aryl groups.

In another embodiment, X, Y, L, $Z^1$, $Z^2$, $Z^3$, $R^1$, and $R^2$ have any of the values of previous embodiments, and $R^3$ is selected from the group consisting of substituted and unsubstituted cyclohexyl, 2-alkylcyclohexyl, 2,2-dialkylcyclohexyl, 2,3-dialkylcyclohexyl, 2,4-dialkylcyclohexyl, 2,5-dialkylcyclohexyl, 2,6-dialkylcyclohexyl, 3,4-dialkylcyclohexyl, 3-alkylcyclohexyl, 4-alkylcyclohexyl, 3,3,5-trialkylcyclohexyl, cyclohexylmethyl, 2-aminocyclohexyl, 3-aminocyclohexyl, 4-aminocyclohexyl, 2,3-diaminocyclohexyl, 2,4-diaminocyclohexyl, 3,4-diaminocyclohexyl, 2,5-diaminocyclohexyl, 2,6-diaminocyclohexyl, 2,2-diaminocyclohexyl, 2-alkoxycyclohexyl, 3-alkoxycyclohexyl, 4-alkoxycyclohexyl, 2,3-dialkoxycyclohexyl, 2,4-dialkoxycyclohexyl, 3,4-dialkoxycyclohexyl, 2,5-dialkoxycyclohexyl, 2,6-dialkoxycyclohexyl, 2,2-dialkoxycyclohexyl, 2-alkylthiocyclohexyl, 3-alkylthiocyclohexyl, 4-alkylthiocyclohexyl, 2,3-dialkylthiocyclohexyl, 2,4-dialkylthiocyclohexyl, 3,4-dialkylthiocyclohexyl, 2,5-dialkylthiocyclohexyl, 2,6-dialkylthiocyclohexyl, 2,2-dialkylthiocyclohexyl, cyclopentyl, cycloheptyl, cyclohexenyl, isopropyl, n-butyl, cyclooctyl, 2-arylcyclohexyl, 2-phenylcyclohexyl, 2-arylalkylcyclohexyl, 2-benzylcyclohexyl, 4-phenylcyclohexyl, adamantyl, isocamphenyl, carenyl, 7,7-dialkylnorbornyl, bornyl, norbornyl, and decalinyl groups.

In another embodiment, X, Y, L, $Z^1$, $Z^2$, $Z^3$, $R^1$, and $R^2$ have any of the values of previous embodiments, and $R^3$ is selected from the group consisting of substituted and unsubstituted cyclohexyl, 2-methylcyclohexyl, 2,2-dimethylcyclohexyl, 2,3-dimethylcyclohexyl, 2,4-dimethylcyclohexyl, 2,5-dimethylcyclohexyl, 2,6-dimethylcyclohexyl, 3,4-dimethylcyclohexyl, 3-methylcyclohexyl, 4-methylcyclohexyl, cyclohex-3-enyl, 3,3,5-trimethylcyclohexyl, 4-t-butylcyclohexyl, 2-methylcycloheptyl, cyclohexylmethyl, isopinocampheyl, 7,7-dimethyinorbornyl, 4-isopropylcyclohexyl, 2,6,6-trimethylbicyclo[3.1.1]heptyl, and 3-methylcycloheptyl.

In another embodiment, X, Y, L, $Z^1$, $Z^2$, $Z^3$, $R^1$, $R^2$, and $R^3$ have any of the values of previous embodiments, and $R^5$ is selected from the group consisting of substituted and unsubstituted alkyl, alkenyl, alkynyl, cycloalkyl, aryl, heteroaryl, heterocyclyl, arylalkyl, heteroarylalkyl, and cycloalkylalkyl groups.

In another embodiment, X, Y, L, $Z^1$, $Z^2$, $Z^3$, $R^1$, $R^2$, and $R^3$ have any of the values of previous embodiments, $R^4$ is H, and $R^5$ is selected from the group consisting of substituted and unsubstituted alkyl, arylalkyl, and heteroarylalkyl groups.

In another embodiment, X, Y, L, $Z^1$, $Z^2$, $Z^3$, $R^1$, $R^2$, and $R^3$ have any of the values of previous embodiments, $R^4$ is H, and $R^5$ is selected from the group consisting of substituted and unsubstituted dialkylaminoethyl, 4-ethylbenzyl, 3-chlorobenzyl, 2,4-dichlorobenzyl, 3-methylbenzyl, benzyl, 4-fluorobenzyl, 3-methoxybenzyl, 2-chorobenzyl, and thiophene groups.

In another embodiment, X, Y, L, $Z^1$, $Z^2$, $Z^3$, $R^1$, $R^2$, and $R^3$ have any of the values of previous embodiments, and $R^4$ and $R^5$ may be the same or different and are each independently selected from the group consisting of substituted and unsubstituted alkyl, arylalkyl, and heteroarylalkyl groups.

In another embodiment, X, Y, L, $Z^1$, $Z^2$, $Z^3$, $R^1$, $R^2$, and $R^3$ have any of the values of previous embodiments, and $R^4$ and $R^5$ may be the same or different and are each independently selected from the group consisting of substituted and unsubstituted dialkylaminoethyl, 4-ethylbenzyl, 3-chlorobenzyl, 2,4-dichlorobenzyl, 3-methylbenzyl, benzyl, 4-fluorobenzyl, 3-methoxybenzyl, 2-chlorobenzyl, and thiophene groups.

In another embodiment, X, Y, L, $Z^1$, $Z^2$, $Z^3$, $R^1$, $R^2$, and $R^3$ have any of the values of previous embodiments, and $R^4$ and $R^5$, together with the nitrogen to which they are bound, form a substituted or unsubstituted piperazino, morpholino, pyrrolidino, piperidino, homopiperazino, or azepino group.

In another embodiment, X, Y, L, $Z^1$, $Z^2$, $Z^3$, $R^1$, $R^2$, and $R^3$ have any of the values of previous embodiments, and $R^4$ and $R^5$, together with the nitrogen to which they are bound, form a piperazino group optionally substituted by one or two alkyl groups, for example, one or two methyl groups.

There has also been provided, in accordance with another aspect of the invention, a compound of formula II:

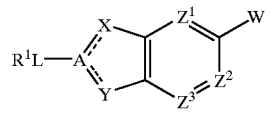

II wherein
A is selected from the group consisting of C or CH;
X and Y are independently selected from the group consisting of $CH_2$, N, C=O, C=S, $(CR^6R^7)_n$, S=O, $SO_2$, O, $NR^9$, S, C(=O)—$(CR^6R^7)_n$, and C(=S)—$(CR^6R^7)_n$;
n is 1, 2, or 3;
W is selected from the group consisting of

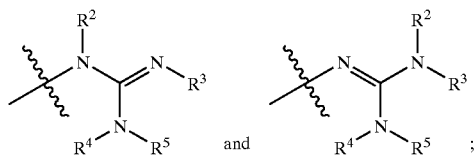

$Z^1$, $Z^2$, and $Z^3$ are independently selected from the group consisting of $CR^8$ and N;
L is selected from the group consisting of N, O, S, S=O, $SO_2$, C(O), NC(O), NC(S), OC(O), OC(S), $C(NR^{10})$, $C(NOR^{10})$, and a covalent bond;
$R^1$ is selected from the group consisting of H, and substituted and unsubstituted arylalkyl, heteroarylalkyl, aryl, heterocyclyl, cycloalkyl, heterocyclylalkyl, cycloalkylalkyl, alkenyl, alkynyl, and alkyl groups;

$R^2$ is selected from the group consisting of H, and substituted and unsubstituted alkyl, alkenyl, alkynyl, cycloalkylalkyl, aryl, and arylalkyl groups;

$R^3$ is selected from the group consisting of H, and substituted and unsubstituted alkyl, alkenyl, alkynyl, cycloalkyl, heteroaryl, heterocyclyl, heterocyclylalkyl, arylalkyl, heteroarylalkyl, and cycloalkylalkyl groups, or $R^2$ and $R^3$ may join together to form a ring containing at least two N atoms;

$R^4$ is selected from the group consisting of H, and substituted and unsubstituted alkyl, alkenyl, alkynyl, cycloalkyl, aryl, heteroaryl, heterocyclyl, arylalkyl, heteroarylalkyl, and cycloalkylalkyl groups, or $R^2$ and $R^4$ may join together to form a ring containing at least two N atoms;

$R^5$ is selected from the group consisting of H, and substituted and unsubstituted alkyl, alkenyl, alkynyl, cycloalkyl, aryl, heteroaryl, heterocyclyl, arylalkyl, heteroarylalkyl, and cycloalkylalkyl groups, or, $R^4$ and $R^5$, together with the nitrogen to which they are bound, form a substituted or unsubstituted heterocyclyl or heteroaryl group, or $R^3$ and $R^5$ may join together to form a ring containing at least two N atoms;

$R^6$ and $R^7$ may be the same or different, and are each independently selected from the group consisting of H, Cl, I, F, Br, OH, $NH_2$, CN, $NO_2$, and substituted and unsubstituted alkoxy, amino, alkyl, alkenyl, alkynyl, alkylamino, dialkylamino, cycloalkyl, heterocyclylamino, heteroarylamino, aminocarbonyl, alkylaminocarbonyl, dialkylaminocarbonyl, cycloalkylaminocarbonyl, arylaminocarbonyl, heterocyclylaminocarbonyl, and heteroarylaminocarbonyl groups;

$R^8$ is independently selected from the group consisting of H, Cl, I, F, Br, OH, $NH_2$, CN, $NO_2$, and substituted and unsubstituted alkoxy, amino, alkyl, alkenyl, alkynyl, alkylamino, dialkylamino, cycloalkyl, heterocyclylamino, heteroarylamino, aminocarbonyl, alkylaminocarbonyl, dialkylaminocarbonyl, cycloalkylaminocarbonyl, arylaminocarbonyl, heterocyclylaminocarbonyl, and heteroarylaminocarbonyl groups; and $R^9$ and $R^{10}$ are independently selected from the group consisting of H, and substituted and unsubstituted alkyl, alkenyl, alkynyl, cycloalkyl, aryl, heteroaryl, heterocyclyl, arylalkyl, heteroarylalkyl, cycloalkylalkyl, alkylcarbonyl, and arylcarbonyl groups.

Compounds provided by the invention further include prodrugs of the compound of formula II, pharmaceutically acceptable salts thereof, stereoisomers thereof, tautomers thereof, hydrates thereof, hydrides thereof, or solvates thereof.

In one embodiment, X is N, Y is NH, A is C, and the bond between X and A is a double bond.

In another embodiment, X is NH, Y is N, A is C, and the bond between Y and A is a double bond.

In another embodiment, A is C and the bond between either A and X or between A and Y is a double bond.

In another embodiment, X, Y, and A have any of the values of previous embodiments, and L is a covalent bond.

In another embodiment, X, Y, A, and L have any of the values of previous embodiments, and $Z^1$, $Z^2$, and $Z^3$ are all CH.

In another embodiment, X, Y, A, and L have any of the values of previous embodiments, and at least one of $Z^1$, $Z^2$, or $Z^3$ is N.

In another embodiment, X, Y, A, L, $Z^1$, $Z^2$, and $Z^3$ have any of the values of previous embodiments, and $R^1$ is selected from the group consisting of substituted and unsubstituted arylalkyl, alkenyl, heteroarylalkyl, and heterocyclylalkyl groups.

In another embodiment, X, Y, A, L, $Z^1$, $Z^2$, and $Z^3$ have any of the values of previous embodiments, and $R^1$ is 2,4-disubstituted phenethyl.

In another embodiment, X, Y, A, L, $Z^1$, $Z^2$, and $Z^3$ have any of the values of previous embodiments, and $R^1$ is selected from the group consisting of 2,4-dihalophenethyl, and 2,4-dialkylphenethyl.

In another embodiment, X, Y, A, L, $Z^1$, $Z^2$, and $Z^3$ have any of the values of previous embodiments, and $R^1$ is selected from the group consisting of phenethyl, 2,4-dichlorophenethyl, 4-methoxyphenethyl, 4-bromophenethyl, 4-methylphenethyl, 4-chlorophenethyl, 4-chlorobenzyl, 4-ethylphenethyl, cyclohexenylethyl, 2-methoxyphenethyl, 2-chlorophenethyl, 2-fluorophenethyl, 3-methoxyphenethyl, 3-fluorophenethyl, thienylethyl, indolylethyl, 4-hydroxyphenethyl, and 3,4-dimethoxyphenethyl.

In another embodiment, X, Y, A, L, $Z^1$, $Z^2$, $Z^3$, and $R^1$ have any of the values of previous embodiments, and $R^2$ is H.

In another embodiment, X, Y, A, L, $Z^1$, $Z^2$, $Z^3$, $R^1$, and $R^2$ have any of the values of previous embodiments, and $R^3$ is selected from the group consisting of substituted and unsubstituted alkyl, alkenyl, alkynyl, cycloalkyl, heteroaryl, heterocyclyl, heterocyclylalkyl, arylalkyl, heteroarylalkyl, and cycloalkylalkyl groups.

In another embodiment, X, Y, A, L, $Z^1$, $Z^2$, $Z^3$, $R^1$, and $R^2$ have any of the values of previous embodiments, and $R^3$ is selected from the group consisting of substituted and unsubstituted cycloalkyl, alkenyl, alkyl, and aryl groups.

In another embodiment, X, Y, A, L, $Z^1$, $Z^2$, $Z^3$, $R^1$, and $R^2$ have any of the values of previous embodiments, and $R^3$ is selected from the group consisting of substituted and unsubstituted cyclohexyl, 2-alkylcyclohexyl, 2,2-dialkylcyclohexyl, 2,3-dialkylcyclohexyl, 2,4-dialkylcyclohexyl, 2,5-dialkylcyclohexyl, 2,6-dialkylcyclohexyl, 3,4-dialkylcyclohexyl, 3-alkylcyclohexyl, 4-alkylcyclohexyl, 3,3,5-trialkylcyclohexyl, cyclohexylmethyl, 2-aminocyclohexyl, 3-aminocyclohexyl, 4-aminocyclohexyl, 2,3-diaminocyclohexyl, 2,4-diaminocyclohexyl, 3,4-diaminocyclohexyl, 2,5-diaminocyclohexyl, 2,6-diaminocyclohexyl, 2,2-diaminocyclohexyl, 2-alkoxycyclohexyl, 3-alkoxycyclohexyl, 4-alkoxycyclohexyl, 2,3-dialkoxycyclohexyl, 2,4-dialkoxycyclohexyl, 3,4-dialkoxycyclohexyl, 2,5-dialkoxycyclohexyl, 2,6-dialkoxycyclohexyl, 2,2-dialkoxycyclohexyl, 2-alkylthiocyclohexyl, 3-alkylthiocyclohexyl, 4-alkylthiocyclohexyl, 2,3-dialkylthiocyclohexyl, 2,4-dialkylthiocyclohexyl, 3,4-dialkylthiocyclohexyl, 2,5-dialkylthiocyclohexyl, 2,6-dialkylthiocyclohexyl, 2,2-dialkylthiocyclohexyl, cyclopentyl, cycloheptyl, cyclohexenyl, isopropyl, n-butyl, cyclooctyl, 2-arylcyclohexyl, 2-phenylcyclohexyl, 2-arylalkylcyclohexyl, 2-benzylcyclohexyl, 4-phenylcyclohexyl, adamantyl, isocamphenyl, carenyl, 7,7-dialkylnorbornyl, bornyl, norbornyl, and decalinyl groups.

In another embodiment, X, Y, A, L, $Z^1$, $Z^2$, $Z^3$, $R^1$, and $R^2$ have any of the values of previous embodiments, and $R^3$ is selected from the group consisting of substituted and unsubstituted cyclohexyl, 2-methylcyclohexyl, 2,2-dimethylcyclohexyl, 2,3-dimethylcyclohexyl, 2,4-dimethylcyclohexyl, 2,5-dimethylcyclohexyl, 2,6-dimethylcyclohexyl, 3,4-dimethylcyclohexyl, 3-methylcyclohexyl, 4-methylcyclohexyl, cyclohex-3-enyl, 3,3,5-trimethylcyclohexyl, 4-t-butylcyclohexyl, 2-methylcycloheptyl, cyclohexylmethyl, isopinocampheyl, 7,7-dimethylnorbornyl, 4-isopropylcyclohexyl, 2,6,6-trimethylbicyclo[3.1.1]heptyl, and 3-methylcycloheptyl.

In another embodiment, X, Y, A, L, $Z^1$, $Z^2$, $Z^3$, $R^1$, $R^2$ and $R^3$ have any of the values of previous embodiments, and $R^5$ is selected from the group consisting of substituted and unsubstituted alkyl, alkenyl, alkynyl, cycloalkyl, aryl, heteroaryl, heterocyclyl, arylalkyl, heteroarylalkyl, and cycloalkylalkyl groups.

In another embodiment, X, Y, A, L, $Z^1$, $Z^2$, $Z^3$, $R^1$, $R^2$ and $R^3$ have any of the values of previous embodiments, $R^4$ is H, and $R^5$ is selected from the group consisting of substituted and unsubstituted alkyl, arylalkyl, and heteroarylalkyl groups.

In another embodiment, X, Y, A, L, $Z^1$, $Z^2$, $Z^3$, $R^1$, $R^2$ and $R^3$ have any of the values of previous embodiments, $R^4$ is H, and $R^5$ is selected from the group consisting of substituted and unsubstituted dialkylaminoethyl, 4-ethylbenzyl, 3-chlorobenzyl, 2,4-dichlorobenzyl, 3-methylbenzyl, benzyl, 4-fluorobenzyl, 3-methoxybenzyl, 2-chlorobenzyl, and thiophene groups.

In another embodiment, X, Y, A, L, $Z^1$, $Z^2$, $Z^3$, $R^1$, $R^2$ and $R^3$ have any of the values of previous embodiments, and $R^4$ and $R^5$ may be the same or different and are each independently selected from the group consisting of substituted and unsubstituted alkyl, arylalkyl, and heteroarylalkyl groups.

In another embodiment, X, Y, A, L, $Z^1$, $Z^2$, $Z^3$, $R^1$, $R^2$ and $R^3$ have any of the values of previous embodiments, and $R^4$ and $R^5$ may be the same or different and are each independently selected from the group consisting of substituted and unsubstituted dialkylaminoethyl, 4-ethylbenzyl, 3-chlorobenzyl, 2,4-dichlorobenzyl, 3-methylbenzyl, benzyl, 4-fluorobenzyl, 3-methoxybenzyl, 2-chlorobenzyl, and thiophene groups.

In another embodiment, X, Y, A, L, $Z^1$, $Z^2$, $Z^3$, $R^1$, $R^2$ and $R^3$ have any of the values of previous embodiments, and $R^4$ and $R^5$, together with the nitrogen to which they are bound, form a substituted or unsubstituted piperazino, morpholino, pyrrolidino, piperidino, homopiperazino, or azepino group.

In another embodiment, X, Y, A, L, $Z^1$, $Z^2$, $Z^3$, $R^1$, $R^2$ and $R^3$ have any of the values of previous embodiments, and $R^4$ and $R^5$, together with the nitrogen to which they are bound, form a piperazino group optionally substituted by one or two alkyl groups, for example, one or two methyl groups.

There has also been provided, in accordance with another aspect of the invention, a compound of formula III:

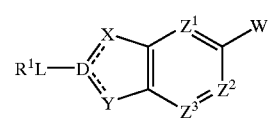

wherein

X and Y are independently selected from the group consisting of $CH_2$, N, C=O, $NR^9$, C=S, S=O, $SO_2$, O, S, $(CR^6R^7)_n$, C(=O)—$(CR^6R^7)_n$, and C(=S)—$(CR^6R^7)_n$;

D is selected from the group consisting of N, and C;

If X is N, then Y is not N, but may be NH;
If Y is N, then X is not N, but may be NH;
If X is CH$_2$, then Y is not CH$_2$;
If Y is CH$_2$, then X is not CH$_2$;
If X is NH, then Y is not NH;
If Y is NH, then X is not NH;

L is selected from the group consisting of N, O, S, S=O, SO$_2$, C(O), NC(O), NC(S), OC(O), OC(S), C(NR$^{10}$), C(NOR$^{10}$), and a covalent bond;

W is selected from the group consisting of

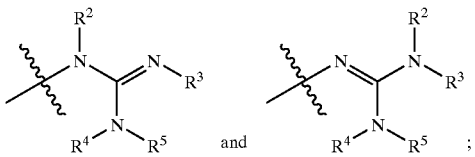

Z$^1$, Z$^2$, and Z$^3$ are independently selected from the group consisting of CR$^8$ and N;

R$^1$ is selected from the group consisting of H, and substituted and unsubstituted arylalkyl, heteroarylalkyl, aryl, heteroaryl, heterocyclyl, cycloalkyl, heterocyclylalkyl, cycloalkylalkyl, alkenyl, alkynyl, and alkyl groups;

R$^2$ is selected from the group consisting of H, and substituted and unsubstituted alkyl, alkenyl, alkynyl, cycloalkylalkyl, aryl, and arylalkyl groups;

R$^3$ is selected from the group consisting of H, and substituted and unsubstituted alkyl, alkenyl, alkynyl, cycloalkyl, heteroaryl, heterocyclyl, heterocyclylalkyl, arylalkyl, heteroarylalkyl, and cycloalkylalkyl groups, or R$^2$ and R$^3$ may join together to form a ring containing at least two N atoms;

R$^4$ is selected from the group consisting of H, and substituted and unsubstituted alkyl, alkenyl, alkynyl, cycloalkyl, aryl, heteroaryl, heterocyclyl, arylalkyl, heteroarylalkyl, and cycloalkylalkyl groups, or R$^2$ and R$^4$ may join together to form a ring containing at least two N atoms;

R$^5$ is selected from the group consisting of H, and substituted and unsubstituted alkyl, alkenyl, alkynyl, cycloalkyl, aryl, heteroaryl, heterocyclyl, arylalkyl, heteroarylalkyl, and cycloalkylalkyl groups, or R$^4$ and R$^5$, together with the nitrogen to which they are bound, form a substituted or unsubstituted heterocyclyl or heteroaryl group, or R$^3$ and R$^5$ may join together to form a ring containing at least two N atoms;

R$^6$ and R$^7$ may be the same or different, and are each independently selected from the group consisting of H, Cl, I, F, Br, OH, NH$_2$, CN, NO$_2$, and substituted and unsubstituted alkoxy, amino, alkyl, alkenyl, alkynyl, alkylamino, dialkylamino, cycloalkyl, heterocyclylamino, heteroarylamino, aminocarbonyl, alkylaminocarbonyl, dialkylaminocarbonyl, cycloalkylaminocarbonyl, arylaminocarbonyl, heterocyclylaminocarbonyl, and heteroarylaminocarbonyl groups;

R$^8$ is independently selected from the group consisting of H, Cl, I, F, Br, OH, NH$_2$, CN, NO$_2$, and substituted and unsubstituted alkoxy, amino, alkyl, alkenyl, alkynyl, alkylamino, dialkylamino, cycloalkyl, heterocyclylamino, heteroarylamino, aminocarbonyl, alkylaminocarbonyl, dialkylaminocarbonyl, cycloalkylaminocarbonyl, arylaminocarbonyl, heterocyclylaminocarbonyl, and heteroarylaminocarbonyl groups; and R$^9$ and R$^{10}$ are independently selected from the group consisting of H, and substituted and unsubstituted alkyl, alkenyl, alkynyl, cycloalkyl, aryl, heteroaryl, heterocyclyl, arylalkyl, heteroarylalkyl, cycloalkylalkyl, alkylcarbonyl, and arylcarbonyl groups.

Compounds provided by the invention further include prodrugs of the compound of formula III, pharmaceutically acceptable salts thereof, stereoisomers thereof, tautomers thereof, hydrates thereof, hydrides thereof, or solvates thereof.

In one embodiment, X is CH$_2$, Y is C=O, and D is N.
In another embodiment, X is C=O, Y is CH$_2$, and D is N.
In another embodiment, X is C=O, Y is C=O, and D is N.
In another embodiment, X is N, Y is NH, D is C, and the bond between X and D is a double bond.
In another embodiment, X is NH, Y is N, D is C, and the bond between Y and D is a double bond.
In another embodiment, X, Y, and D have any of the values of previous embodiments, and L is a covalent bond.
In another embodiment, X, Y, D, and L have any of the values of previous embodiments, and Z$^1$, Z$^2$, and Z$^3$ are all CH.
In another embodiment, X, Y, D, and L have any of the values of previous embodiments, and at least one of Z$^1$, Z$^2$, or Z$^3$ is N.
In another embodiment, X, Y, D, L, Z$^1$, Z$^2$, and Z$^3$ have any of the values of previous embodiments, and R$^1$ is selected from the group consisting of substituted and unsubstituted arylalkyl, alkenyl, heteroarylalkyl, and heterocyclylalkyl groups.
In another embodiment, X, Y, D, L, Z$^1$, Z$^2$, and Z$^3$ have any of the values of previous embodiments, and R$^1$ is 2,4-disubstituted phenethyl.
In another embodiment, X, Y, D, L, Z$^1$, Z$^2$, and Z$^3$ have any of the values of previous embodiments, and R$^1$ is selected from the group consisting of 2,4-dihalophenethyl, and 2,4-dialkylphenethyl.
In another embodiment, X, Y, D, L, Z$^1$, Z$^2$, and Z$^3$ have any of the values of previous embodiments, and R$^1$ is selected from the group consisting of phenethyl, 2,4-dichlorophenethyl, 4-methoxyphenethyl, 4-bromophenethyl, 4-methylphenethyl, 4-chlorophenethyl, 4-chlorobenzyl, 4-ethylphenethyl, cyclohexenylethyl, 2-methoxyphenethyl, 2-chlorophenethyl, 2-fluorophenethyl, 3-methoxyphenethyl, 3-fluorophenethyl, thienylethyl, indolylethyl, 4-hydroxyphenethyl, and 3,4-dimethoxyphenethyl.
In another embodiment, X, Y, D, L, Z$^1$, Z$^2$, Z$^3$, and R$^1$ have any of the values of previous embodiments, and R$^2$ is H.
In another embodiment, X, Y, D, L, Z$^1$, Z$^2$, Z$^3$, R$^1$, and R$^2$ have any of the values of previous embodiments, and R$^3$ is selected from the group consisting of substituted and unsubstituted alkyl, alkenyl, alkynyl, cycloalkyl, heteroaryl, heterocyclyl, heterocyclylalkyl, arylalkyl, heteroarylalkyl, and cycloalkylalkyl groups.
In another embodiment, X, Y, D, L, Z$^1$, Z$^2$, Z$^3$, R$^1$, and R$^2$ have any of the values of previous embodiments, and R$^3$ is selected from the group consisting of substituted and unsubstituted cycloalkyl, alkenyl, alkyl, and aryl groups.
In another embodiment, X, Y, D, L, Z$^1$, Z$^2$, Z$^3$, R$^1$, and R$^2$ have any of the values of previous embodiments, and R$^3$ is selected from the group consisting of substituted and unsubstituted cyclohexyl, 2-alkylcyclohexyl, 2,2-dialkylcyclohexyl, 2,3-dialkylcyclohexyl, 2,4-dialkylcyclohexyl, 2,5-dialkylcyclohexyl, 2,6-dialkylcyclohexyl, 3,4-dialkylcyclohexyl, 3-alkylcyclohexyl, 4-alkylcyclohexyl, 3,3,5-trialkylcyclohexyl, cyclohexylmethyl, 2-aminocyclohexyl, 3-aminocyclohexyl, 4-aminocyclohexyl, 2,3-diaminocyclohexyl, 2,4-diaminocyclohexyl, 3,4-diaminocyclohexyl, 2,5-diaminocyclohexyl, 2,6-diaminocyclohexyl, 2,2-diaminocyclohexyl, 2-alkoxycyclohexyl, 3-alkoxycyclohexyl, 4-alkoxycyclohexyl, 2,3-dialkoxycyclohexyl, 2,4-dialkoxycyclohexyl, 3,4-dialkoxycyclohexyl, 2,5-dialkoxycyclohexyl, 2,6-dialkoxycyclohexyl, 2,2-dialkoxycyclohexyl, 2-alkylthiocyclohexyl, 3-alkylthiocyclohexyl, 4-alkylthiocyclohexyl, 2,3-dialkylthiocyclohexyl, 2,4-dialkylthiocyclohexyl, 3,4-dialkylthiocyclohexyl, 2,5-dialkylthiocyclohexyl, 2,6-dialkylthiocyclohexyl, 2,2-dialkylthiocyclohexyl, cyclopentyl, cycloheptyl, cyclohexenyl, isopropyl, n-butyl, cyclooctyl, 2-arylcyclohexyl, 2-phenylcyclohexyl, 2-arylalkylcyclohexyl, 2-benzylcyclohexyl, 4-phenylcyclohexyl, adamantyl, isocamphenyl, carenyl, 7,7-dialkylnorbornyl, bornyl, norbornyl, and decalinyl groups.

In another embodiment, X, Y, D, L, $Z^1, Z^2, Z^3, R^1$, and $R^2$ have any of the values of previous embodiments, and $R^3$ is selected from the group consisting of substituted and unsubstituted cyclohexyl, 2-methylcyclohexyl, 2,2-dimethylcyclohexyl, 2,3-dimethylcyclohexyl, 2,4-dimethylcyclohexyl, 2,5-dimethylcyclohexyl, 2,6-dimethylcyclohexyl, 3,4-dimethylcyclohexyl, 3-methylcyclohexyl, 4-methylcyclohexyl, cyclohex-3-enyl, 3,3,5-trimethylcyclohexyl, 4-t-butylcyclohexyl, 2-methylcycloheptyl, cyclohexylmethyl, isopinocampheyl, 7,7-dimethyinorbornyl, 4-isopropylcyclohexyl, 2,6,6-trimethylbicyclo[3.1.1]heptyl, and 3-methylcycloheptyl.

In another embodiment, X, Y, D, L, $Z^1, Z^2, Z^3, R^1, R^2$ and $R^3$ have any of the values of previous embodiments, and $R^5$ is selected from the group consisting of substituted and unsubstituted alkyl, alkenyl, alkynyl, cycloalkyl, aryl, heteroaryl, heterocyclyl, arylalkyl, heteroarylalkyl, and cycloalkylalkyl groups.

In another embodiment, X, Y, D, L, $Z^1, Z^2, Z^3, R^1, R^2$ and $R^3$ have any of the values of previous embodiments, $R^4$ is H, and $R^5$ is selected from the group consisting of substituted and unsubstituted alkyl, arylalkyl, and heteroarylalkyl groups.

In another embodiment, X, Y, D, L, $Z^1, Z^2, Z^3, R^1, R^2$ and $R^3$ have any of the values of previous embodiments, $R^4$ is H, and $R^5$ is selected from the group consisting of substituted and unsubstituted dialkylaminoethyl, 4-ethylbenzyl, 3-chlorobenzyl, 2,4-dichlorobenzyl, 3-methylbenzyl, benzyl, 4-fluorobenzyl, 3-methoxybenzyl, 2-chlorobenzyl, and thiophene groups.

In another embodiment, X, Y, D, L, $Z^1, Z^2, Z^3, R^1, R^2$ and $R^3$ have any of the values of previous embodiments, and $R^4$ and $R^5$ may be the same or different and are each independently selected from the group consisting of substituted and unsubstituted alkyl, arylalkyl, and heteroarylalkyl groups.

In another embodiment, X, Y, D, L, $Z^1, Z^2, Z^3, R^1, R^2$ and $R^3$ have any of the values of previous embodiments, and $R^4$ and $R^5$ may be the same or different and are each independently selected from the group consisting of substituted and unsubstituted dialkylaminoethyl, 4-ethylbenzyl, 3-chlorobenzyl, 2,4-dichlorobenzyl, 3-methylbenzyl, benzyl, 4-fluorobenzyl, 3-methoxybenzyl, 2-chlorobenzyl, and thiophene groups.

In another embodiment, X, Y, D, L, $Z^1, Z^2, Z^3, R^1, R^2$ and $R^3$ have any of the values of previous embodiments, and $R^4$ and $R^5$, together with the nitrogen to which they are bound, form a substituted or unsubstituted piperazino, morpholino, pyrrolidino, piperidino, homopiperazino, or azepino group.

In another embodiment, X, Y, D, L, $Z^1, Z^2, Z^3, R^1, R^2$ and $R^3$ have any of the values of previous embodiments, and $R^4$ and $R^5$, together with the nitrogen to which they are bound, form a piperazino group optionally substituted by one or two alkyl groups, for example, one or two methyl groups.

There has also been provided, in accordance with another aspect of the invention, a composition comprising a compound according to the instant invention and a pharmaceutically acceptable carrier.

There has also been provided, in accordance with another aspect of the invention, a method of activating MC4-R, comprising administering to a subject in need thereof, an effective amount of a compound or composition of the instant invention.

There has also been provided, in accordance with another aspect of the invention, a method of treating an MC4-R mediated disease, comprising administering to a subject in need thereof, a compound or composition of the instant invention.

In one embodiment, a disease to be treated by those methods of the instant invention is obesity, or type I or type II diabetes.

There has also been provided, in accordance with another aspect of the invention, a method of decreasing blood glucose levels, comprising administering to a subject in need thereof, a compound or composition of the instant invention.

In various alternative embodiments, the composition is administered orally, rectally, by subcutaneous injection, by intravenous injection, by intramuscular injection, or by intraperitoneal injection.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENT

The instant invention relates to novel classes of small molecule melanocortin-4 receptor (MC4-R) agonists. These compounds can be formulated into compositions and are useful in activating MC4-R, or in the treatment of MC4-R-mediated diseases, such as obesity.

The following definitions are used throughout this specification:

Alkyl groups are straight chain lower alkyl groups having 1 to about 8 carbon atoms, as exemplified by methyl, ethyl, propyl, butyl, pentyl, hexyl, heptyl, and octyl. Alkyl groups also include branched chain isomers of straight chain alkyl groups, including, but not limited to, isopropyl, sec-butyl, t-butyl, isopentyl and so on. Representative substituted alkyl groups may be substituted one or more times with, for example, amino, thio, alkoxy, or halo.

Cycloalkyl groups are cyclic alkyl groups such as, but not limited to, cyclopropyl, cyclobutyl, cyclopentyl, cyclohexyl, cycloheptyl, and cyclooctyl groups, and can include two or more bridgehead carbon atoms to form polycyclic rings (e.g., norbornyl or bicyclo[3.1.1]heptyl). Cycloalkyl groups also includes rings that are substituted with straight or branched chain alkyl groups as defined above (e.g., bornyl or 2,6,6-trimethylbicyclo[3.1.1]heptyl). Representative substituted cycloalkyl groups may be mono-substituted or substituted more than once, such as, but not limited to, 2,2-, 2,3-, 2,4- 2,5- or 2,6-disubstituted cyclohexyl groups or mono-, di- or tri-substituted norbornyl or cycloheptyl groups, which may be substituted with, for example, alkyl, alkoxy, amino, thio, or halo groups.

Alkenyl groups are straight chain, branched or cyclic lower alkyl groups having 2 to about 8 carbon atoms, and further including at least one double bond, as exemplified, for instance, by vinyl, propenyl, 2-butenyl, 3-butenyl, isobutenyl, cyclohexenyl, cyclopentenyl, cyclohexadienyl, butadienyl, pentadienyl, and hexadienyl groups among others.

Alkynyl groups are straight chain or branched lower alkyl groups having 2 to about 8 carbon atoms, and further including at least one triple bond, as exemplified by groups, including, but not limited to, ethynyl, propynyl, and butynyl groups.

Aryl groups are cyclic aromatic hydrocarbons that do not contain heteroatoms. Thus aryl groups include, but are not limited to, phenyl, azulene, heptalene, biphenylene, indacene, fluorene, phenanthrene, triphenylene, pyrene, naphthacene, chrysene, biphenyl, anthracenyl, and naphthenyl groups. Although the phrase "aryl groups" includes groups containing fused rings, such as fused aromatic-aliphatic ring systems, it does not include aryl groups that have other groups, such as alkyl or halo groups, bonded to one of the ring members. Rather, groups such as tolyl are referred to as substituted aryl groups. The phrase "aryl groups" includes groups bonded to one or more carbon atom(s), and/or nitrogen atom(s), in the compounds of formulas I and II. Representative substituted aryl groups may be mono-substituted or substituted more than once, such as, but not limited to, 2-, 3-, 4-, 5-, or 6-substituted phenyl or benzyl groups, which may be substituted with groups including, but not limited to, amino, alkoxy, alkyl, or halo.

Cycloalkylalkyl groups are alkyl groups as defined above in which a hydrogen or carbon bond of an alkyl group is replaced with a bond to a cycloalkyl group as defined above.

Arylalkyl groups are alkyl groups as defined above in which a hydrogen or carbon bond of an alkyl group is replaced with a bond to an aryl group as defined above.

Heterocyclyl groups are nonaromatic ring compounds containing 3 or more ring members, of which, one or more is a heteroatom such as, but not limited to, N, O, and S. The phrase "heterocyclyl group" includes fused ring species including those comprising fused aromatic and nonaromatic groups. However, the phrase does not include heterocyclyl groups that have other groups, such as alkyl or halo groups, bonded to one of the ring members. Rather, these are referred to as "substituted heterocyclyl groups". Heterocyclyl groups include, but are not limited to, piperazino, morpholino, thiomorpholino, pyrrolidino, piperidino and homopiperazino groups. Representative substituted heterocyclyl groups may be mono-substituted or substituted more than once, such as, but not limited to morphilino or piperazino groups, which are 2-, 3-, 4-, 5-, or 6-substituted, or disubstituted with groups including, but not limited to, amino, alkoxy, alkyl, or halo.

Heteroaryl groups are aromatic ring compounds containing 3 or more ring members, of which, one or more is a heteroatom such as, but not limited to, N, O, and S. Heteroaryl groups include, but are not limited to, groups such as furan, thiophene, pyrrole, isopyrrole, diazole, imidazole, isoimidazole, triazole, dithiole, oxathiole, isoxazole, oxazole, thiazole, isothiazole, oxadiazole, oxatriazole, dioxazole, oxathiazole, pyran, dioxin, pyridine, pyrimidine, pyridazine, pyrazine, triazine, oxazine, isoxazine, oxathiazine, azepin, oxepin, thiepin, diazepine, benzofuran, and isobenzofuran. Although the phrase "heteroaryl groups" includes fused ring compounds, the phrase does not include heteroaryl groups that have other groups bonded to one of the ring members, such as alkyl groups. Rather, heteroaryl groups with such substitution are referred to as "substituted heterocyclyl groups". Representative substituted heterocyclyl groups may be substituted one or more times with groups including, but not limited to, amino, alkoxy, alkyl, or halo.

Heterocyclylalkyl groups are alkyl groups as defined above in which a hydrogen or carbon bond of an alkyl group is replaced with a bond to a heterocyclyl group as defined above.

Heteroarylalkyl groups are alkyl groups as defined above in which a hydrogen or carbon bond of an alkyl group is replaced with a bond to a heteroaryl group as defined above.

Aminocarbonyl groups are groups of the formula RR'NC (O)—, wherein R or R' may be the same or different, and each is independently selected from H, or substituted or unsubstituted alkyl, cycloalkyl, aryl, heterocyclyl or heteroaryl groups, as defined above.

In general, "substituted" refers to a group as defined above in which one or more bonds to a hydrogen atom contained therein are replaced by a bond to non-hydrogen or non-carbon atoms such as, but not limited to, a halogen atom such as F, Cl, Br, and I; an oxygen atom in groups such as hydroxyl groups, alkoxy groups, aryloxy groups, and ester groups; a sulfur atom in groups such as thiol groups, alkyl and aryl sulfide groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as in trialkylsilyl groups, dialkylarylsilyl groups, alkyldiarylsilyl groups, and triarylsilyl groups; and other heteroatoms in various other groups. Substituted alkyl groups and also substituted cycloalkyl groups also include groups in which one or more bonds to a carbon(s) or hydrogen(s) atom is replaced by a bond to a heteroatom such as oxygen in carbonyl, carboxyl, and ester groups; nitrogen in groups such as imines, oximes, hydrazones, and nitriles.

Substituted cycloalkyl, substituted aryl, substituted heterocyclyl and substituted heteroaryl also include rings and fused ring systems which may be substituted with alkyl groups as defined above. Substituted arylalkyl groups may be substituted on the aryl group, on the alkyl group, or on both the aryl and alkyl groups.

The instant invention provides potent and specific agonists of MC4-R that are low molecular weight non-peptide small molecules. Thus, there has been provided, in accordance with one aspect of the invention, a compound of formula I:

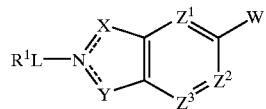

wherein

X and Y are independently selected from the group consisting of $CH_2$, N, $NR^9$, C=O, C=S, S=O, $SO_2$, S, O, $(CR^6R^7)_n$, $C(=O)-(CR^6R^7)_n$, and $C(=S)-(CR^6R^7)_n$;

n is 1, 2, or 3;

W is selected from the group consisting of

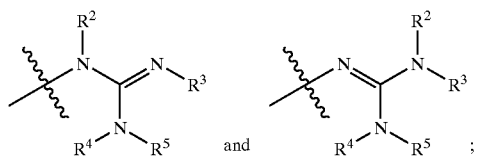

L is selected from the group consisting of N, O, S, S=O, $SO_2$, C(O), NC(O), NC(S), OC(O), OC(S), $C(NR^{10})$, $C(NOR^{10})$, and a covalent bond;

$Z^1$, $Z^2$, and $Z^3$ are independently selected from the group consisting of $CR^8$ and N;

$R^1$ is selected from the group consisting of H, and substituted and unsubstituted arylalkyl, heteroarylalkyl, aryl, heteroaryl, heterocyclyl, cycloalkyl, heterocyclylalkyl, cycloalkylalkyl, alkenyl, alkynyl, and alkyl groups;

$R^2$ is selected from the group consisting of H, and substituted and unsubstituted alkyl, alkenyl, alkynyl, cycloalkylalkyl, aryl, and arylalkyl groups;

$R^3$ is selected from the group consisting of H, and substituted and unsubstituted alkyl, alkenyl, alkynyl, cycloalkyl, heteroaryl, heterocyclyl, heterocyclylalkyl, arylalkyl, heteroarylalkyl, and cycloalkylalkyl groups, or $R^2$ and $R^3$ may join together to form a ring containing at least two N atoms;

$R^4$ is selected from the group consisting of H, and substituted and unsubstituted alkyl, alkenyl, alkynyl, cycloalkyl, aryl, heteroaryl, heterocyclyl, arylalkyl, heteroarylalkyl, and cycloalkylalkyl groups, or $R^2$ and $R^4$ may join together to form a ring containing at least two N atoms;

$R^5$ is selected from the group consisting of H, and substituted and unsubstituted alkyl, alkenyl, alkynyl, cycloalkyl, aryl, heteroaryl, heterocyclyl, arylalkyl, heteroarylalkyl, and cycloalkylalkyl groups, or $R^4$ and $R^5$, together with the nitrogen to which they are bound, form a substituted or unsubstituted heterocyclyl or heteroaryl group, or $R^3$ and $R^5$ may join together to form a ring containing at least two N atoms;

$R^6$ and $R^7$ may be the same or different, and are each independently selected from the group consisting of H, Cl, I, F, Br, OH, $NH_2$, CN, $NO_2$, and substituted and unsubstituted alkoxy, amino, alkyl, alkenyl, alkynyl, alkylamino, dialkylamino, cycloalkyl, heterocyclylamino, heteroarylamino, aminocarbonyl, alkylaminocarbonyl, dialkylaminocarbonyl, cycloalkylaminocarbonyl, arylaminocarbonyl, heterocyclylaminocarbonyl, and heteroarylaminocarbonyl groups;

$R^8$ is independently selected from the group consisting of H, Cl, I, F, Br, OH, $NH_2$, CN, $NO_2$, and substituted and unsubstituted alkoxy, amino, alkyl, alkenyl, alkynyl, alkylamino, dialkylamino, cycloalkyl, heterocyclylamino, heteroarylamino, aminocarbonyl, alkylaminocarbonyl, dialkylaminocarbonyl, cycloalkylaminocarbonyl, arylaminocarbonyl, heterocyclylaminocarbonyl, and heteroarylaminocarbonyl groups; and $R^9$ and $R^{10}$ are independently selected from the group consisting of H, and substituted and unsubstituted alkyl, alkenyl, alkynyl, cycloalkyl, aryl, heteroaryl, heterocyclyl, arylalkyl, heteroarylalkyl, cycloalkylalkyl, alkylcarbonyl, and arylcarbonyl groups.

Compounds provided by the invention further include prodrugs of the compound of formula I, pharmaceutically acceptable salts thereof, stereoisomers thereof, tautomers thereof, hydrates thereof, hydrides thereof, or solvates thereof.

In one embodiment, X is $CH_2$ and Y is C=O.

In another embodiment, X is C=O and Y is $CH_2$.

In another embodiment, X is C=O and Y is C=O.

In other embodiments, L is a covalent bond, and X and Y have the values according to any of the previous embodiments.

In another embodiment, $Z^1$, $Z^2$, and $Z^3$ are all CH, and X, Y, and L have the values according to any of the previous embodiments.

In another embodiment, at least one of $Z^1$, $Z^2$, or $Z^3$ is N, and X, Y, and L have the values according to any of the previous embodiments.

In another embodiment, X, Y, L, $Z^1$, $Z^2$, and $Z^3$ have any of the values of previous embodiments, and $R^1$ is selected from the group consisting of substituted and unsubstituted arylalkyl, alkenyl, heteroarylalkyl, and heterocyclylalkyl groups.

In another embodiment, X, Y, L, $Z^1$, $Z^2$, and $Z^3$ have any of the values of previous embodiments, and $R^1$ is 2,4-disubstituted phenethyl.

In another embodiment, X, Y, L, $Z^1$, $Z^2$, and $Z^3$ have any of the values of previous embodiments, and $R^1$ is selected from the group consisting of 2,4-dihalophenethyl, and 2,4-dialkylphenethyl.

In another embodiment, X, Y, L, $Z^1$, $Z^2$, and $Z^3$ have any of the values of previous embodiments, and $R^1$ is selected from the group consisting of phenethyl, 2,4-dichlorophenethyl, 4-methoxyphenethyl, 4-bromophenethyl, 4-methylphenethyl, 4-chlorophenethyl, 4-chlorobenzyl, 4-ethylphenethyl, cyclohexenylethyl, 2-methoxyphenethyl, 2-chlorophenethyl, 2-fluorophenethyl, 3-methoxyphenethyl, 3-fluorophenethyl, thienylethyl, indolylethyl, 4-hydroxyphenethyl, and 3,4-dimethoxyphenethyl.

In another embodiment, X, Y, L, $Z^1$, $Z^2$, $Z^3$, and $R^1$ have any of the values of previous embodiments, and $R^2$ is H.

In another embodiment, X, Y, L, $Z^1$, $Z^2$, $Z^3$, $R^1$, and $R^2$ have any of the values of previous embodiments, and $R^3$ is selected from the group consisting of substituted and unsubstituted alkyl, alkenyl, alkynyl, cycloalkyl, heteroaryl, heterocyclyl, heterocyclylalkyl, arylalkyl, heteroarylalkyl, and cycloalkylalkyl groups.

In another embodiment, X, Y, L, $Z^1$, $Z^2$, $Z^3$, $R^1$, and $R^2$ have any of the values of previous embodiments, and $R^3$ is selected from the group consisting of substituted and unsubstituted cycloalkyl, alkenyl, alkyl, and aryl groups.

In another embodiment, X, Y, L, $Z^1$, $Z^2$, $Z^3$, $R^1$, and $R^2$ have any of the values of previous embodiments, and $R^3$ is selected from the group consisting of substituted and unsubstituted cyclohexyl, 2-alkylcyclohexyl, 2,2-dialkylcyclohexyl, 2,3-dialkylcyclohexyl, 2,4-dialkylcyclohexyl, 2,5-dialkylcyclohexyl, 2,6-dialkylcyclohexyl, 3,4-dialkylcyclohexyl, 3-alkylcyclohexyl, 4-alkylcyclohexyl, 3,3,5-trialkylcyclohexyl, cyclohexylmethyl, 2-aminocyclohexyl, 3-aminocyclohexyl, 4-aminocyclohexyl, 2,3-diaminocyclohexyl, 2,4-diaminocyclohexyl, 3,4-diaminocyclohexyl, 2,5-diaminocyclohexyl, 2,6-diaminocyclohexyl, 2,2-diaminocyclohexyl, 2-alkoxycyclohexyl, 3-alkoxycyclohexyl, 4-alkoxycyclohexyl, 2,3-dialkoxycyclohexyl, 2,4-dialkoxycyclohexyl, 3,4-dialkoxycyclohexyl, 2,5-dialkoxycyclohexyl, 2,6-dialkoxycyclohexyl, 2,2-dialkoxycyclohexyl, 2-alkylthiocyclohexyl, 3-alkylthiocyclohexyl, 4-alkylthiocyclohexyl, 2,3-dialkylthiocyclohexyl, 2,4-dialkylthiocyclohexyl, 3,4-dialkylthiocyclohexyl, 2,5-dialkythiocyclohexyl, 2,6-dialkylthiocyclohexyl, 2,2-dialkylthiocyclohexyl, cyclopentyl, cycloheptyl, cyclohexenyl, isopropyl, n-butyl, cyclooctyl, 2-arylcyclohexyl, 2-phenylcyclohexyl, 2-arylalkylcyclohexyl, 2-benzylcyclohexyl, 4-phenylcyclohexyl, adamantyl, isocamphenyl, carenyl, 7,7-dialkylnorbornyl, bornyl, norbornyl, and decalinyl groups.

In another embodiment, X, Y, L, $Z^1$, $Z^2$, $Z^3$, $R^1$, and $R^2$ have any of the values of previous embodiments, and $R^3$ is selected from the group consisting of substituted and unsubstituted cyclohexyl, 2-methylcyclohexyl, 2,2-dimethylcyclohexyl, 2,3-dimethylcyclohexyl, 2,4-dimethylcyclohexyl, 2,5-dimethylcyclohexyl, 2,6-dimethylcyclohexyl, 3,4-dimethylcyclohexyl, 3-methylcyclohexyl, 4-methylcyclohexyl, cyclohex-3-enyl, 3,3,5-trimethylcyclohexyl, 4-t-butylcyclohexyl, 2-methylcycloheptyl, cyclohexylmethyl, isopinocampheyl, 7,7-dimethyinorbornyl, 4-isopropylcyclohexyl, 2,6,6-trimethylbicyclo[3.1.1]heptyl, and 3-methylcycloheptyl.

In another embodiment, X, Y, L, $Z^1$, $Z^2$, $Z^3$, $R^1$, $R^2$, and $R^3$ have any of the values of previous embodiments, and $R^5$ is selected from the group consisting of substituted and unsubstituted alkyl, alkenyl, alkynyl, cycloalkyl, aryl, heteroaryl, heterocyclyl, arylalkyl, heteroarylalkyl, and cycloalkylalkyl groups.

In another embodiment, X, Y, L, $Z^1$, $Z^2$, $Z^3$, $R^1$, $R^2$, and $R^3$ have any of the values of previous embodiments, $R^4$ is H, and $R^5$ is selected from the group consisting of substituted and unsubstituted alkyl, arylalkyl, and heteroarylalkyl groups.

In another embodiment, X, Y, L, $Z^1$, $Z^2$, $Z^3$, $R^1$, $R^2$, and $R^3$ have any of the values of previous embodiments, $R^4$ is H, and $R^5$ is selected from the group consisting of substituted and unsubstituted dialkylaminoethyl, 4-ethylbenzyl, 3-chlorobenzyl, 2,4-dichlorobenzyl, 3-methylbenzyl, benzyl, 4-fluorobenzyl, 3-methoxybenzyl, 2-chlorobenzyl, and thiophene groups.

In another embodiment, X, Y, L, $Z^1$, $Z^2$, $Z^3$, $R^1$, $R^2$, and $R^3$ have any of the values of previous embodiments, and $R^4$ and $R^5$ may be the same or different and are each independently selected from the group consisting of substituted and unsubstituted alkyl, arylalkyl, and heteroarylalkyl groups.

In another embodiment, X, Y, L, $Z^1$, $Z^2$, $Z^3$, $R^1$, $R^2$, and $R^3$ have any of the values of previous embodiments, and $R^4$ and $R^5$ may be the same or different and are each independently selected from the group consisting of substituted and unsubstituted dialkylaminoethyl, 4-ethylbenzyl, 3-chlorobenzyl, 2,4-dichlorobenzyl, 3-methylbenzyl, benzyl, 4-fluorobenzyl, 3-methoxybenzyl, 2-chlorobenzyl, and thiophene groups.

In another embodiment, X, Y, L, $Z^1$, $Z^2$, $Z^3$, $R^1$, $R^2$, and $R^3$ have any of the values of previous embodiments, and $R^4$ and $R^5$, together with the nitrogen to which they are bound, form a substituted or unsubstituted piperazino, morpholino, pyrrolidino, piperidino, homopiperazino, or azepino group.

In another embodiment, X, Y, L, $Z^1$, $Z^2$, $Z^3$, $R^1$, $R^2$, and $R^3$ have any of the values of previous embodiments, and $R^4$ and $R^5$, together with the nitrogen to which they are bound, form a piperazino group optionally substituted by one or two alkyl groups, for example, one or two methyl groups.

There has also been provided, in accordance with another aspect of the invention, a compound of formula II:

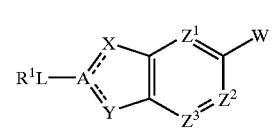

II wherein

A is selected from the group consisting of C or CH;

X and Y are independently selected from the group consisting of $CH_2$, N, C=O, C=S, $(CR^6R^7)_n$, S=O, $SO_2$, O, $NR^9$, S, C(=O)—$(CR^6R^7)_n$, and C(=S)—$(CR^6R^7)_n$;

n is 1, 2, or 3;

W is selected from the group consisting of

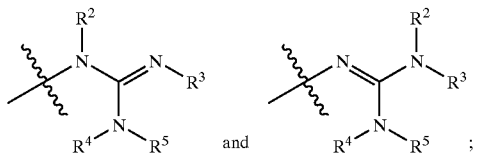

and

;

$Z^1$, $Z^2$, and $Z^3$ are independently selected from the group consisting of $CR^8$ and N;

L is selected from the group consisting of N, O, S, S=O, $SO_2$, C(O), NC(O), NC(S), OC(O), OC(S), $C(NR^{10})$, $C(NOR^{10})$, and a covalent bond;

$R^1$ is selected from the group consisting of H, and substituted and unsubstituted arylalkyl, heteroarylalkyl, aryl, heterocyclyl, cycloalkyl, heterocyclylalkyl, cycloalkylalkyl, alkenyl, alkynyl, and alkyl groups;

$R^2$ is selected from the group consisting of H, and substituted and unsubstituted alkyl, alkenyl, alkynyl, cycloalkylalkyl, aryl, and arylalkyl groups;

$R^3$ is selected from the group consisting of H, and substituted and unsubstituted alkyl, alkenyl, alkynyl, cycloalkyl, heteroaryl, heterocyclyl, heterocyclylalkyl, arylalkyl, heteroarylalkyl, and cycloalkylalkyl groups, or $R^2$ and $R^3$ may join together to form a ring containing at least two N atoms;

$R^4$ is selected from the group consisting of H, and substituted and unsubstituted alkyl, alkenyl, alkynyl, cycloalkyl, aryl, heteroaryl, heterocyclyl, arylalkyl, heteroarylalkyl, and cycloalkylalkyl groups, or $R^2$ and $R^4$ may join together to form a ring containing at least two N atoms;

$R^5$ is selected from the group consisting of H, and substituted and unsubstituted alkyl, alkenyl, alkynyl, cycloalkyl, aryl, heteroaryl, heterocyclyl, arylalkyl, heteroarylalkyl, and cycloalkylalkyl groups, or $R^4$ and $R^5$, together with the nitrogen to which they are bound, form a substituted or unsubstituted heterocyclyl or heteroaryl group, or $R^3$ and $R^5$ may join together to form a ring containing at least two N atoms;

$R^6$ and $R^7$ may be the same or different, and are each independently selected from the group consisting of H, Cl, I, F, Br, OH, $NH_2$, CN, $NO_2$, and substituted and unsubstituted alkoxy, amino, alkyl, alkenyl, alkynyl, alkylamino, dialkylamino, cycloalkyl, heterocyclylamino, heteroarylamino, aminocarbonyl, alkylaminocarbonyl, dialkylaminocarbonyl, cycloalkylaminocarbonyl, arylaminocarbonyl, heterocyclylaminocarbonyl, and heteroarylaminocarbonyl groups;

$R^8$ is independently selected from the group consisting of H, Cl, I, F, Br, OH, $NH_2$, CN, $NO_2$, and substituted and unsubstituted alkoxy, amino, alkyl, alkenyl, alkynyl, alkylamino, dialkylamino, cycloalkyl, heterocyclylamino, heteroarylamino, aminocarbonyl, alkylaminocarbonyl, dialkylaminocarbonyl, cycloalkylaminocarbonyl, arylaminocarbonyl, heterocyclylaminocarbonyl, and heteroarylaminocarbonyl groups; and $R^9$ and $R^{10}$ are independently selected from the group consisting of H, and substituted and unsubstituted alkyl, alkenyl, alkynyl, cycloalkyl, aryl, heteroaryl, heterocyclyl, arylalkyl, heteroarylalkyl, cycloalkylalkyl, alkylcarbonyl, and arylcarbonyl groups.

Compounds provided by the invention further include prodrugs of the compound of formula II, pharmaceutically acceptable salts thereof, stereoisomers thereof, tautomers thereof, hydrates thereof, hydrides thereof, or solvates thereof.

In one embodiment, X is N, Y is NH, A is C, and the bond between X and A is a double bond.

In another embodiment, X is NH, Y is N, A is C, and the bond between Y and A is a double bond.

In another embodiment, A is C and the bond between either A and X or between A and Y is a double bond.

In another embodiment, X, Y, and A have any of the values of previous embodiments, and L is a covalent bond.

In another embodiment, X, Y, A, and L have any of the values of previous embodiments, and $Z^1$, $Z^2$, and $Z^3$ are all CH.

In another embodiment, X, Y, A, and L have any of the values of previous embodiments, and at least one of $Z^1$, $Z^2$, or $Z^3$ is N.

In another embodiment, X, Y, A, L, $Z^1$, $Z^2$, and $Z^3$ have any of the values of previous embodiments, and $R^1$ is selected from the group consisting of substituted and unsubstituted arylalkyl, alkenyl, heteroarylalkyl, and heterocyclylalkyl groups.

In another embodiment, X, Y, A, L, $Z^1$, $Z^2$, and $Z^3$ have any of the values of previous embodiments, and $R^1$ is 2,4-disubstituted phenethyl.

In another embodiment, X, Y, A, L, $Z^1$, $Z^2$, and $Z^3$ have any of the values of previous embodiments, and $R^1$ is selected from the group consisting of 2,4-dihalophenethyl, and 2,4-dialkylphenethyl.

In another embodiment, X, Y, A, L, $Z^1$, $Z^2$, and $Z^3$ have any of the values of previous embodiments, and $R^1$ is selected from the group consisting of phenethyl, 2,4-dichlorophenethyl, 4-methoxyphenethyl, 4-bromophenethyl, 4-methylphenethyl, 4-chlorophenethyl, 4-chlorobenzyl, 4-ethylphenethyl, cyclohexenylethyl, 2-methoxyphenethyl, 2-chlorophenethyl, 2-fluorophenethyl, 3-methoxyphenethyl, 3-fluorophenethyl, thienylethyl, indolylethyl, 4-hydroxyphenethyl, and 3,4-dimethoxyphenethyl.

In another embodiment, X, Y, A, L, $Z^1$, $Z^2$, $Z^3$, and $R^1$ have any of the values of previous embodiments, and $R^2$ is H.

In another embodiment, X, Y, A, L, $Z^1$, $Z^2$, $Z^3$, $R^1$, and $R^2$ have any of the values of previous embodiments, and $R^3$ is selected from the group consisting of substituted and unsubstituted alkyl, alkenyl, alkynyl, cycloalkyl, heteroaryl, heterocyclyl, heterocyclylalkyl, arylalkyl, heteroarylalkyl, and cycloalkylalkyl groups.

In another embodiment, X, Y, A, L, $Z^1$, $Z^2$, $Z^3$, $R^1$, and $R^2$ have any of the values of previous embodiments, and $R^3$ is selected from the group consisting of substituted and unsubstituted cycloalkyl, alkenyl, alkyl, and aryl groups.

In another embodiment, X, Y, A, L, $Z^1$, $Z^2$, $Z^3$, $R^1$, and $R^2$ have any of the values of previous embodiments, and $R^3$ is selected from the group consisting of substituted and unsubstituted cyclohexyl, 2-alkylcyclohexyl, 2,2-dialkylcyclohexyl, 2,3-dialkylcyclohexyl, 2,4-dialkylcyclohexyl, 2,5-dialkylcyclohexyl, 2,6-dialkylcyclohexyl, 3,4-dialkylcyclohexyl, 3-alkylcyclohexyl, 4-alkylcyclohexyl, 3,3,5-trialkylcyclohexyl, cyclohexylmethyl, 2-aminocyclohexyl, 3-aminocyclohexyl, 4-aminocyclohexyl, 2,3-diaminocyclohexyl, 2,4-diaminocyclohexyl, 3,4-diaminocyclohexyl, 2,5-diaminocyclohexyl, 2,6-diaminocyclohexyl, 2,2-diaminocyclohexyl, 2-alkoxycyclohexyl, 3-alkoxycyclohexyl, 4-alkoxycyclohexyl, 2,3-dialkoxycyclohexyl, 2,4-dialkoxycyclohexyl, 3,4-dialkoxycyclohexyl, 2,5-dialkoxycyclohexyl, 2,6-dialkoxycyclohexyl, 2,2-dialkoxycyclohexyl, 2-alkyithiocyclohexyl, 3-alkylthiocyclohexyl, 4-alkylthiocyclohexyl, 2,3-dialkylthiocyclohexyl, 2,4-dialkylthiocyclohexyl, 3,4-dialkylthiocyclohexyl, 2,5-dialkylthiocyclohexyl, 2,6-dialkylthiocyclohexyl, 2,2-dialkylthiocyclohexyl, cyclopentyl, cycloheptyl, cyclohexenyl, isopropyl, n-butyl, cyclooctyl, 2-arylcyclohexyl, 2-phenylcyclohexyl, 2-arylalkylcyclohexyl, 2-benzylcyclohexyl, 4-phenylcyclohexyl, adamantyl, isocamphenyl, carenyl, 7,7-dialkylnorbornyl, bornyl, norbornyl, and decalinyl groups.

In another embodiment, X, Y, A, L, $Z^1$, $Z^2$, $Z^3$, $R^1$, and $R^2$ have any of the values of previous embodiments, and $R^3$ is selected from the group consisting of substituted and unsubstituted cyclohexyl, 2-methylcyclohexyl, 2,2-dimethylcyclohexyl, 2,3-dimethylcyclohexyl, 2,4-dimethylcyclohexyl, 2,5-dimethylcyclohexyl, 2,6-dimethylcyclohexyl, 3,4-dimethylcyclohexyl, 3-methylcyclohexyl, 4-methylcyclohexyl, cyclohex-3-enyl, 3,3,5-trimethylcyclohexyl, 4-t-butylcyclohexyl, 2-methylcycloheptyl, cyclohexylmethyl, isopinocampheyl, 7,7-dimethyinorbornyl, 4-isopropylcyclohexyl, 2,6,6-trimethylbicyclo[3.1.1]heptyl, and 3-methylcycloheptyl.

In another embodiment, X, Y, A, L, $Z^1$, $Z^2$, $Z^3$, $R^1$, $R^2$ and $R^3$ have any of the values of previous embodiments, and $R^5$ is selected from the group consisting of substituted and unsubstituted alkyl, alkenyl, alkynyl, cycloalkyl, aryl, heteroaryl, heterocyclyl, arylalkyl, heteroarylalkyl, and cycloalkylalkyl groups.

In another embodiment, X, Y, A, L, $Z^1$, $Z^2$, $Z^3$, $R^1$, $R^2$ and $R^3$ have any of the values of previous embodiments, $R^4$ is H, and $R^5$ is selected from the group consisting of substituted and unsubstituted alkyl, arylalkyl, and heteroarylalkyl groups.

In another embodiment, X, Y, A, L, $Z^1$, $Z^2$, $Z^3$, $R^1$, $R^2$ and $R^3$ have any of the values of previous embodiments, $R^4$ is H, and $R^5$ is selected from the group consisting of substituted and unsubstituted dialkylaminoethyl, 4-ethylbenzyl, 3-chlorobenzyl, 2,4-dichlorobenzyl, 3-methylbenzyl, benzyl, 4-fluorobenzyl, 3-methoxybenzyl, 2-chlorobenzyl, and thiophene groups.

In another embodiment, X, Y, A, L, $Z^1$, $Z^2$, $Z^3$, $R^1$, $R^2$ and $R^3$ have any of the values of previous embodiments, and $R^4$ and $R^5$ may be the same or different and are each independently selected from the group consisting of substituted and unsubstituted alkyl, arylalkyl, and heteroarylalkyl groups.

In another embodiment, X, Y, A, L, $Z^1$, $Z^2$, $Z^3$, $R^1$, $R^2$ and $R^3$ have any of the values of previous embodiments, and $R^4$ and $R^5$ may be the same or different and are each independently selected from the group consisting of substituted and unsubstituted dialkylaminoethyl, 4-ethylbenzyl, 3-chlorobenzyl, 2,4-dichlorobenzyl, 3-methylbenzyl, benzyl, 4-fluorobenzyl, 3-methoxybenzyl, 2-chlorobenzyl, and thiophene groups.

In another embodiment, X, Y, A, L, $Z^1$, $Z^2$, $Z^3$, $R^1$, $R^2$ and $R^3$ have any of the values of previous embodiments, and $R^4$ and $R^5$, together with the nitrogen to which they are bound, form a substituted or unsubstituted piperazino, morpholino, pyrrolidino, piperidino, homopiperazino, or azepino group.

In another embodiment, X, Y, A, L, $Z^1$, $Z^2$, $Z^3$, $R^1$, $R^2$ and $R^3$ have any of the values of previous embodiments, and $R^4$ and $R^5$, together with the nitrogen to which they are bound, form a piperazino group optionally substituted by one or two alkyl groups, for example, one or two methyl groups.

There has also been provided, in accordance with another aspect of the invention, a compound of formula III:

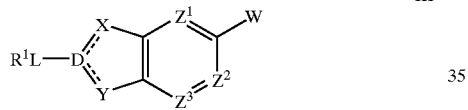

III wherein
X and Y are independently selected from the group consisting of $CH_2$, N, C=O, $NR^9$, C=S, S=O, $SO_2$, O, S, $(CR^6R^7)_n$, C(=O)—$(CR^6R^7)_n$, and C(=S)—$(CR^6R^7)_n$;

D is selected from the group consisting of N, and C;
If X is N, then Y is not N, but may be NH;
If Y is N, then X is not N, but may be NH;
If X is $CH_2$, then Y is not $CH_2$;
If Y is $CH_2$, then X is not $CH_2$;
If X is NH, then Y is not NH;
If Y is NH, then X is not NH;
L is selected from the group consisting of N, O, S, S=O, $SO_2$, C(O), NC(O), NC(S), OC(O), OC(S), C($NR^{10}$), C($NOR^{10}$), and a covalent bond;
W is selected from the group consisting of

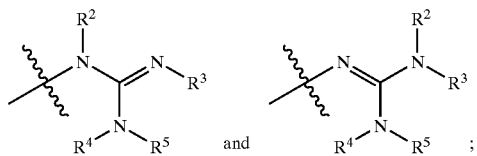

$Z^1$, $Z^2$, and $Z^3$ are independently selected from the group consisting of $CR^8$ and N;
$R^1$ is selected from the group consisting of H, and substituted and unsubstituted arylalkyl, heteroarylalkyl, aryl, heteroaryl, heterocyclyl, cycloalkyl, heterocyclylalkyl, cycloalkylalkyl, alkenyl, alkynyl, and alkyl groups;
$R^2$ is selected from the group consisting of H, and substituted and unsubstituted alkyl, alkenyl, alkynyl, cycloalkylalkyl, aryl, and arylalkyl groups;
$R^3$ is selected from the group consisting of H, and substituted and unsubstituted alkyl, alkenyl, alkynyl, cycloalkyl, heteroaryl, heterocyclyl, heterocyclylalkyl, arylalkyl, heteroarylalkyl, and cycloalkylalkyl groups, or $R^2$ and $R^3$ may join together to form a ring containing at least two N atoms;
$R^4$ is selected from the group consisting of H, and substituted and unsubstituted alkyl, alkenyl, alkynyl, cycloalkyl, aryl, heteroaryl, heterocyclyl, arylalkyl, heteroarylalkyl, and cycloalkylalkyl groups, or $R^2$ and $R^4$ may join together to form a ring containing at least two N atoms;
$R^5$ is selected from the group consisting of H, and substituted and unsubstituted alkyl, alkenyl, alkynyl, cycloalkyl, aryl, heteroaryl, heterocyclyl, arylalkyl, heteroarylalkyl, and cycloalkylalkyl groups, or $R^4$ and $R^5$, together with the nitrogen to which they are bound, form a substituted or unsubstituted heterocyclyl or heteroaryl group, or $R^3$ and $R^5$ may join together to form a ring containing at least two N atoms;
$R^6$ and $R^7$ may be the same or different, and are each independently selected from the group consisting of H, Cl, I, F, Br, OH, $NH_2$, CN, $NO_2$, and substituted and unsubstituted alkoxy, amino, alkyl, alkenyl, alkynyl, alkylamino, dialkylamino, cycloalkyl, heterocyclylamino, heteroarylamino, aminocarbonyl, alkylaminocarbonyl, dialkylaminocarbonyl, cycloalkylaminocarbonyl, arylaminocarbonyl, heterocyclylaminocarbonyl, and heteroarylaminocarbonyl groups;
$R^8$ is independently selected from the group consisting of H, Cl, I, F, Br, OH, $NH_2$, CN, $NO_2$, and substituted and unsubstituted alkoxy, amino, alkyl, alkenyl, alkynyl, alkylamino, dialkylamino, cycloalkyl, heterocyclylamino, heteroarylamino, aminocarbonyl, alkylaminocarbonyl, dialkylaminocarbonyl, cycloalkylaminocarbonyl, arylaminocarbonyl, heterocyclylaminocarbonyl, and heteroarylaminocarbonyl groups; and
$R^9$ and $R^{10}$ are independently selected from the group consisting of H, and substituted and unsubstituted alkyl, alkenyl, alkynyl, cycloalkyl, aryl, heteroaryl, heterocyclyl, arylalkyl, heteroarylalkyl, cycloalkylalkyl, alkylcarbonyl, and arylcarbonyl groups.

Compounds provided by the invention further include prodrugs of the compound of formula III, pharmaceutically acceptable salts thereof, stereoisomers thereof, tautomers thereof, hydrates thereof, hydrides thereof, or solvates thereof.

In one embodiment, X is $CH_2$, Y is C=O, and D is N.
In another embodiment, X is C=O, Y is $CH_2$, and D is N.
In another embodiment, X is C=O, Y is C=O, and D is N.
In another embodiment, X is N, Y is NH, D is C, and the bond between X and D is a double bond.
In another embodiment, X is NH, Y is N, D is C, and the bond between Y and D is a double bond.
In another embodiment, X, Y, and D have any of the values of previous embodiments, and L is a covalent bond.

In another embodiment, X, Y, D, and L have any of the values of previous embodiments, and $Z^1$, $Z^2$, and $Z^3$ are all CH.

In another embodiment, X, Y, D, and L have any of the values of previous embodiments, and at least one of $Z^1$, $Z^2$, or $Z^3$ is N.

In another embodiment, X, Y, D, L, $Z^1$, $Z^2$, and $Z^3$ have any of the values of previous embodiments, and $R^1$ is selected from the group consisting of substituted and unsubstituted arylalkyl, alkenyl, heteroarylalkyl, and heterocyclylalkyl groups.

In another embodiment, X, Y, D, L, $Z^1$, $Z^2$, and $Z^3$ have any of the values of previous embodiments, and $R^1$ is 2,4-disubstituted phenethyl.

In another embodiment, X, Y, D, L, $Z^1$, $Z^2$, and $Z^3$ have any of the values of previous embodiments, and $R^1$ is selected from the group consisting of 2,4-dihalophenethyl, and 2,4-dialkylphenethyl.

In another embodiment, X, Y, D, L, $Z^1$, $Z^2$, and $Z^3$ have any of the values of previous embodiments, and $R^1$ is selected from the group consisting of phenethyl, 2,4-dichlorophenethyl, 4-methoxyphenethyl, 4-bromophenethyl, 4-methylphenethyl, 4-chlorophenethyl, 4-chlorobenzyl, 4-ethylphenethyl, cyclohexenylethyl, 2-methoxyphenethyl, 2-chlorophenethyl, 2-fluorophenethyl, 3-methoxyphenethyl, 3-fluorophenethyl, thienylethyl, indolylethyl, 4-hydroxyphenethyl, and 3,4-dimethoxyphenethyl.

In another embodiment; X, Y, D, L, $Z^1$, $Z^2$, $Z^3$, and $R^1$ have any of the values of previous embodiments, and $R^2$ is H.

In another embodiment, X, Y, D, L, $Z^1$, $Z^2$, $Z^3$, $R^1$, and $R^2$ have any of the values of previous embodiments, and $R^3$ is selected from the group consisting of substituted and unsubstituted alkyl, alkenyl, alkynyl, cycloalkyl, heteroaryl, heterocyclyl, heterocyclylalkyl, arylalkyl, heteroarylalkyl, and cycloalkylalkyl groups.

In another embodiment, X, Y, D, L, $Z^1$, $Z^2$, $Z^3$, $R^1$, and $R^2$ have any of the values of previous embodiments, and $R^3$ is selected from the group consisting of substituted and unsubstituted cycloalkyl, alkenyl, alkyl, and aryl groups.

In another embodiment, X, Y, D, L, $Z^1$, $Z^2$, $Z^3$, $R^1$, and $R^2$ have any of the values of previous embodiments, and $R^3$ is selected from the group consisting of substituted and unsubstituted cyclohexyl, 2-alkylcyclohexyl, 2,2-dialkylcyclohexyl, 2,3-dialkylcyclohexyl, 2,4-dialkylcyclohexyl, 2,5-dialkylcyclohexyl, 2,6-dialkylcyclohexyl, 3,4-dialkylcyclohexyl, 3-alkylcyclohexyl, 4-alkylcyclohexyl, 3,3,5-trialkylcyclohexyl, cyclohexylmethyl, 2-aminocyclohexyl, 3-aminocyclohexyl, 4-aminocyclohexyl, 2,3-diaminocyclohexyl, 2,4-diaminocyclohexyl, 3,4-diaminocyclohexyl, 2,5-diaminocyclohexyl, 2,6-diaminocyclohexyl, 2,2-diaminocyclohexyl, 2-alkoxycyclohexyl, 3-alkoxycyclohexyl, 4-alkoxycyclohexyl, 2,3-dialkoxycyclohexyl, 2,4-dialkoxycyclohexyl, 3,4-dialkoxycyclohexyl, 2,5-dialkoxycyclohexyl, 2,6-dialkoxycyclohexyl, 2,2-dialkoxycyclohexyl, 2-alkylthiocyclohexyl, 3-alkylthiocyclohexyl, 4-alkylthiocyclohexyl, 2,3-dialkylthiocyclohexyl, 2,4-dialkylthiocyclohexyl, 3,4-dialkylthiocyclohexyl, 2,5-dialkylthiocyclohexyl, 2,6-dialkylthiocyclohexyl, 2,2-dialkylthiocyclohexyl, cyclopentyl, cycloheptyl, cyclohexenyl, isopropyl, n-butyl, cyclooctyl, 2-arylcyclohexyl, 2-phenylcyclohexyl, 2-arylalkylcyclohexyl, 2-benzylcyclohexyl, 4-phenylcyclohexyl, adamantyl, isocamphenyl, carenyl, 7,7-dialkylnorbornyl, bornyl, norbornyl, and decalinyl groups.

In another embodiment, X, Y, D, L, $Z^1$, $Z^2$, $Z^3$, $R^1$, and $R^2$ have any of the values of previous embodiments, and $R^3$ is selected from the group consisting of substituted and unsubstituted cyclohexyl, 2-methylcyclohexyl, 2,2-dimethylcyclohexyl, 2,3-dimethylcyclohexyl, 2,4-dimethylcyclohexyl, 2,5-dimethylcyclohexyl, 2,6-dimethylcyclohexyl, 3,4-dimethylcyclohexyl, 3-methylcyclohexyl, 4-methylcyclohexyl, cyclohex-3-enyl, 3,3,5-trimethylcyclohexyl, 4-t-butylcyclohexyl, 2-methylcycloheptyl, cyclohexylmethyl, isopinocampheyl, 7,7-dimethylnorbornyl, 4-isopropylcyclohexyl, 2,6,6-trimethylbicyclo[3.1.1]heptyl, and 3-methylcycloheptyl.

In another embodiment, X, Y, D, L, $Z^1$, $Z^2$, $Z^3$, $R^1$, $R^2$ and $R^3$ have any of the values of previous embodiments, and $R^5$ is selected from the group consisting of substituted and unsubstituted alkyl, alkenyl, alkynyl, cycloalkyl, aryl, heteroaryl, heterocyclyl, arylalkyl, heteroarylalkyl, and cycloalkylalkyl groups.

In another embodiment, X, Y, D, L, $Z^1$, $Z^2$, $Z^3$, $R^1$, $R^2$ and $R^3$ have any of the values of previous embodiments, $R^4$ is H, and $R^5$ is selected from the group consisting of substituted and unsubstituted alkyl, arylalkyl, and heteroarylalkyl groups.

In another embodiment, X, Y, D, L, $Z^1$, $Z^2$, $Z^3$, $R^1$, $R^2$ and $R^3$ have any of the values of previous embodiments, $R^4$ is H, and $R^5$ is selected from the group consisting of substituted and unsubstituted dialkylaminoethyl, 4-ethylbenzyl, 3-chlorobenzyl, 2,4-dichlorobenzyl, 3-methylbenzyl, benzyl, 4-fluorobenzyl, 3-methoxybenzyl, 2-chlorobenzyl, and thiophene groups.

In another embodiment, X, Y, D, L, $Z^1$, $Z^2$, $Z^3$, $R^1$, $R^2$ and $R^3$ have any of the values of previous embodiments, and $R^4$ and $R^5$ may be the same or different and are each independently selected from the group consisting of substituted and unsubstituted alkyl, arylalkyl, and heteroarylalkyl groups.

In another embodiment, X, Y, D, L, $Z^1$, $Z^2$, $Z^3$, $R^1$, $R^2$ and $R^3$ have any of the values of previous embodiments, and $R^4$ and $R^5$ may be the same or different and are each independently selected from the group consisting of substituted and unsubstituted dialkylaminoethyl, 4-ethylbenzyl, 3-chlorobenzyl, 2,4-dichlorobenzyl, 3-methylbenzyl, benzyl, 4-fluorobenzyl, 3-methoxybenzyl, 2-chlorobenzyl, and thiophene groups.

In another embodiment, X, Y, D, L, $Z^1$, $Z^2$, $Z^3$, $R^1$, $R^2$ and $R^3$ have any of the values of previous embodiments, and $R^4$ and $R^5$, together with the nitrogen to which they are bound, form a substituted or unsubstituted piperazino, morpholino, pyrrolidino, piperidino, homopiperazino, or azepino group.

In another embodiment, X, Y, D, L, $Z^1$, $Z^2$, $Z^3$, $R^1$, $R^2$ and $R^3$ have any of the values of previous embodiments, and $R^4$ and $R^5$, together with the nitrogen to which they are bound, form a piperazino group optionally substituted by one or two alkyl groups, for example, one or two methyl groups.

There has also been provided, in accordance with another aspect of the invention, a composition comprising a compound according to the instant invention and a pharmaceutically acceptable carrier.

There has also been provided, in accordance with another aspect of the invention, a method of activating MC4-R, comprising administering to a subject in need thereof, an effective amount of a compound or composition of the instant invention.

There has also been provided, in accordance with another aspect of the invention, a method of treating an MC4-R mediated disease, comprising administering to a subject in need thereof, a compound or composition of the instant invention.

In one embodiment, a disease to be treated by those methods of the instant invention is obesity, or type I or type II diabetes.

There has also been provided, in accordance with another aspect of the invention, a method of decreasing blood glucose levels, comprising administering to a subject in need thereof, a compound or composition of the instant invention.

In various alternative embodiments, the composition is administered orally, rectally, by subcutaneous injection, by intravenous injection, by intramuscular injection, or by intraperitoneal injection.

The variables "$(CR^6R^7)_n$", "$C(=O)-(CR^6R^7)_n$", and "$C(=S)-(CR^6R^7)_n$" are used with respect to X and Y in compounds of formula I, II, and III where n has the value of 1, 2, or 3. The variable "$(CR^6R^7)_n$" has the same meaning in compounds of formula I, II, and III. The same is true with respect to the variables "$C(=O)-(CR^6R^7)_n$" and "$C(=S)-(CR^6R^7)_n$". Compounds of formula I will be used to illustrate what these variables mean. In compounds of formula I as shown below

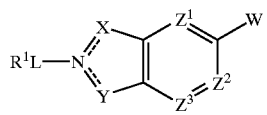

X and Y are independently selected from the group consisting of $CH_2$, N, NH, C=O, C=S, S=O, $SO_2$, O, $(CR^6R^7)_n$, $C(=O)-(CR^6R^7)_n$, and $C(=S)-(CR^6R^7)_n$; and n is 1, 2, or 3 as described above. The variable "$(CR^6R^7)_n$" indicates that X and/or Y may be a one, two, or three carbon chain with the carbons bearing the $R^6$ and $R^7$ groups. Thus, if X is a three carbon chain (n=3) and Y is a one carbon chain, the ring bearing the X, Y and N will contain 7 members. It should be noted that where n=3 and X or Y is a "$(CR^6R^7)_n$" group, the three carbon chain may be substituted where each carbon bears the same $R^6$ and $R^7$ substituents although this is not required. For example, X could be a —$CH_2CH(Cl)C(Cl)_2$— group because $R^6$ and $R^7$ may be H and Cl. Thus, the nomenclature used herein is not meant to restrict each of the carbons to bearing exactly the same substituents as would be the case for n=3 for an X group such as —CH(Cl)—CH(Cl)—CH(Cl)—. This same feature is true with respect to the variables "$C(=O)-(CR^6R^7)_n$" and "$C(=S)-(CR^6R^7)_n$". With respect to the variables "$C(=O)-(CR^6R^7)_n$" and "$C(=S)-(CR^6R^7)_n$", X and/or Y may contain from two to four carbon atoms since n=1, 2, or 3, and the C=O and C=S groups of these species contains one carbon atoms. With respect to the variables "$C(=O)-(CR^6R^7)_n$" and "$C(=S)-(CR^6R^7)_n$", either terminus of the group may be bonded to the N atom in the ring containing the X, Y, and N. Thus, the carbonyl carbon of the $C(=O)-(CR^6R^7)_n$ group may be the carbon directly bonded to the N in the ring, but one of the $CR^6R^7$ carbons may alternatively be bonded to the ring N atom. Preferably, however, it is the C=O and C=S carbons of such groups that is bonded to the ring N atoms.

As described above, in some embodiments L may be a covalent bond. In embodiments where L is a covalent bond, the $R^1$ group is directly bonded to the N in the ring containing the X and Y in compounds of formula I or is directly bonded to A or D in the ring containing the X and Y in compounds of formulas II and III respectively.

Pharmaceutically acceptable salts include a salt with an inorganic base, organic base, inorganic acid, organic acid, or basic or acidic amino acid. As salts of inorganic bases, the invention includes, for example, alkali metals such as sodium or potassium, alkali earth metals such as calcium and magnesium or aluminum, and ammonia. As salts of organic bases, the invention includes, for example, trimethylamine, triethylamine, pyridine, picoline, ethanolamine, diethanolamine, triethanolamine. As salts of inorganic acids, the instant invention includes, for example, hydrochloric acid, hydroboric acid, nitric acid, sulfuric acid, and phosphoric acid. As salts of organic acids, the instant invention includes, for example, formic acid, acetic acid, trifluoroacetic acid, fumaric acid, oxalic acid, tartaric acid, maleic acid, citric acid, succinic acid, malic acid, methanesulfonic acid, benzenesulfonic acid, and p-toluenesulfonic acid. As salts of basic amino acids, the instant invention includes, for example, arginine, lysine and ornithine. Acidic amino acids include, for example, aspartic acid and glutamic acid.

Prodrugs, as used in the context of the instant invention, includes those derivatives of the instant compounds which undergo in vivo metabolic biotransformation, by enzymatic or nonenzymatic processes, such as hydrolysis, to form a compound of the invention. Prodrugs can be employed to improve pharmaceutical or biological properties, as for example solubility, melting point, stability and related physicochemical properties, absorption, pharmacodynamics and other delivery-related properties.

The invention also includes tautomers of the instant compounds. For example, the instant invention also includes all tautomers of formula I, II, and III.

The instant invention also, therefore, includes prodrugs, pharmaceutically acceptable salts, stereoisomers, hydrates, hydrides, or solvates of these tautomers.

The instant compounds may exist as one or more stereoisomers. The various stereoisomers include enantiomers, diastereomers, atropisomers and geometric isomers. In some cases, one stereoisomer may be more active and/or may exhibit beneficial effects in comparison to other stereoisomer(s) or when separated from the other stereoisomer(s). However, it is well within the skill of the ordinary artisan to separate, and/or to selectively prepare said stereoisomers. Accordingly, "stereoisomers" of the instant invention necessarily includes mixtures of stereoisomers, individual stereoisomers, or optically active forms.

The instant invention also provides for compositions which may be prepared by mixing one or more compounds of the instant invention, or pharmaceutically acceptable salts or tautomers thereof, with pharmaceutically acceptable carriers, excipients, binders, diluents or the like, to treat or ameliorate a variety of disorders. Examples of such disorders include, but are not limited to obesity, erectile disorders, cardiovascular disorders, neuronal injuries or disorders, inflammation, fever, cognitive disorders, sexual behavior disorders. A therapeutically effective dose further refers to that amount of one or more compounds of the instant invention sufficient to result in amelioration of symptoms of the disorder. The pharmaceutical compositions of the instant invention can be manufactured by methods well known in the art such as conventional granulating, mixing, dissolving, encapsulating, lyophilizing, emulsifying or levigating processes, among others. The compositions can be in the form of, for example, granules, powders, tablets, capsules, syrup, suppositories, injections, emulsions, elixirs, suspensions or solutions. The instant compositions can be formulated for various routes of administration, for example, by oral administration, by transmucosal administration, by rectal administration, or subcutaneous administration as well as intrathecal, intravenous, intramuscular, intraperitoneal, intranasal, intraocular or intraventricular injection. The compound or compounds of the instant invention can also be administered in a local rather than a systemic fashion, such as injection as a sustained release formulation. The following dosage forms are given by way of example and should not be construed as limiting the instant invention.

For oral, buccal, and sublingual administration, powders, suspensions, granules, tablets, pills, capsules, gelcaps, and caplets are acceptable as solid dosage forms. These can be prepared, for example, by mixing one or more compounds of the instant invention, or pharmaceutically acceptable salts or tautomers thereof, with at least one additive or excipient such as a starch or other additive. Suitable additives or excipients are sucrose, lactose, cellulose sugar, mannitol, maltitol, dextran, sorbitol, starch, agar, alginates, chitins, chitosans, pectins, tragacanth gum, gum arabic, gelatins, collagens, casein, albumin, synthetic or semi-synthetic polymers or glycerides, methyl cellulose, hydroxypropylmethylcellulose, and/or polyvinylpyrrolidone. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, a thickeners, buffers, a sweeteners, flavoring agents or perfuming agents. Additionally, dyestuffs or pigments may be added for identification. Tablets and pills may be further treated with suitable coating materials known in the art.

Liquid dosage forms for oral administration may be in the form of pharmaceutically acceptable emulsions, syrups, elixirs, suspensions, slurries and solutions, which may contain an inactive diluent, such as water. Pharmaceutical formulations may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

As noted above, suspensions may include oils. Such oils include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

For nasal administration, the pharmaceutical formulations may be a spray or aerosol containing and appropriate solvents and optionally other compounds such as, but not limited to, stabilizers, antimicrobial agents, antioxidants, pH modifiers, surfactants, bioavailability modifiers and combinations of these. A propellant for an aerosol formulation may include compressed air, nitrogen, carbon dioxide, or a hydrocarbon based low boiling solvent. The compound or compounds of the instant invention are conveniently delivered in the form of an aerosol spray presentation from a nebulizer or the like.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Preferably, the oil or fatty acid is non-volatile, including natural or synthetic oils, fatty acids, mono-, di- or tri-glycerides.

For injection, the pharmaceutical formulation may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these. The compounds may be formulated for parenteral administration by injection such as by bolus injection or continuous infusion. A unit dosage form for injection may be in ampoules or in multi-dose containers.

For rectal administration, the pharmaceutical formulations may be in the form of a suppository, an ointment, an enema, a tablet or a cream for release of compound in the intestines, sigmoid flexure and/or rectum. Rectal suppositories are prepared by mixing one or more compounds of the instant invention, or pharmaceutically acceptable salts or tautomers of the compound, with acceptable vehicles, for example, cocoa butter or polyethylene glycol, which is present in a solid phase at normal storing temperatures, and present in a liquid phase at those temperatures suitable to release a drug inside the body, such as in the rectum. Oils may also be employed in the preparation of formulations of the soft gelatin type and suppositories. Water, saline, aqueous dextrose and related sugar solutions, and glycerols may be employed in the preparation of suspension formulations which may also contain suspending agents such as pectins, carbomers, methyl cellulose, hydroxypropyl cellulose or carboxymethyl cellulose, as well as buffers and preservatives.

Besides those representative dosage forms described above, pharmaceutically acceptable excipients and carriers are generally known to those skilled in the art and are thus included in the instant invention. Such excipients and carriers are described, for example, in "Remingtons Pharmaceutical Sciences" Mack Pub. Co., New Jersey (1991), which is incorporated herein by reference.

The formulations of the invention may be designed for to be short-acting, fast-releasing, long-acting, and sustained-releasing as described below. Thus, the pharmaceutical formulations may also be formulated for controlled release or for slow release.

The instant compositions may also comprise, for example, micelles or liposomes, or some other encapsulated form, or may be administered in an extended release form to provide a prolonged storage and/or delivery effect. Therefore, the pharmaceutical formulations may be compressed into pellets or cylinders and implanted intramuscularly or subcutaneously as depot injections or as implants such as stents. Such implants may employ known inert materials such as silicones and biodegradable polymers.

A therapeutically effective dose refers to that amount of the compound that results in amelioration of symptoms. Specific dosages may be adjusted depending on conditions of disease, the age, body weight, general health conditions, sex, diet of the subject, dose intervals, administration routes, excretion rate, and combinations of drugs. Any of the above dosage forms containing effective amounts are well within the bounds of routine experimentation and therefore, well within the scope of the instant invention. A therapeutically effective dose may vary depending upon the route of administration and dosage form. The preferred compound or compounds of the instant invention is a formulation that exhibits a high therapeutic index. The therapeutic index is the dose ratio between toxic and therapeutic effects which can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ are determined by standard pharmaceutical procedures in animal cell cultures or experimental animals.

The present invention also provides methods of enhancing MC4-R activity in a human or non-human animal. The method comprises administering an effective amount of a compound, or composition, of the instant invention to said mammal or non-human animal. Effective amounts of the compounds of the instant invention include those amounts that activate MC4-R which are detectable, for example, by an assay described below in the illustrative Examples, or any other assay known by those skilled in the art that a detect signal transduction, in a biochemical pathway, through activation of G-protein coupled receptors, for example, by measuring an elevated cAMP level as compared to a control model. Accordingly, "activating" means the ability of a compound to initiate a detectable signal. Effective amounts may also include those amounts which alleviate symptoms of a MC4-R disorder treatable by activating MC4-R.

An MC4-R disorder, or MC4-R-mediated disease, which may be treated by those methods provided, include any biological disorder or disease in which MC4-R is implicated, or which inhibition of MC4-R potentiates a biochemical pathway that is defective in the disorder or disease state. Examples of such diseases are obesity, erectile disorders, cardiovascular disorders, neuronal injuries or disorders, inflammation, fever, cognitive disorders, and sexual behavior disorders. In a preferred embodiment, the instant invention provides compounds, compositions, and methods effective for reducing energy intake and body weight; reducing serum insulin and glucose levels; alleviating insulin resistance; and reducing serum levels of free fatty acids. Accordingly, the instant invention is particularly effective in treating those disorders or diseases associated with obesity or type II diabetes.

"Treating" within the context of the instant invention, therefore, means an alleviation of symptoms associated with a disorder or disease, or halt of further progression or worsening of those symptoms, or prevention or prophylaxis of the disease or disorder. For example, within the context of obesity, successful treatment may include an alleviation of symptoms or halting the progression of the disease, as measured by reduction in body weight, or a reduction in amount of food or energy intake. In this same vein, successful treatment of type I or type II diabetes may include an alleviation of symptoms or halting the progression of the disease, as measured by a decrease in serum glucose or insulin levels in, for example, hyperinsulinemic or hyperglycemic patients.

Compound Preparation

Many of the described specific synthetic transformation steps are farhiliar to those skilled in the art and their procedures are either described or referenced in common texts such as in March *Advanced Organic Chemistry* 3rd ed. (Wiley, 1985), Carey and Sundberg *Advanced Organic Chemistry* A and B 3rd ed. (Plenum Press, 1990), and Vogel's Textbook of *Practical Organic Chemistry* 5th ed. (Longman, 1989). Implicit in the synthetic transformations are various techniques for purification such as silica gel chromatography, crystallizations, and distillations. These steps may be necessary for isolating the desired product, regioisomer, enantiomer, or diastereomer from a reaction product mixture. Multistep syntheses may also involve the use of protecting groups to address issues of chemo and regioselectivity that cannot otherwise be satisfactorily resolved with respect to chemical purity or yield.

The use of protecting groups in organic synthesis is well known with respect to various groups such as hydroxyl groups, amine groups, and sulfhydryl groups. These and other functionalities may be protected from undesirable reactions with various protecting groups known to those skilled in the art such as those set forth in *Protective Groups in Organic Synthesis,* Greene, T. W., John Wiley & Sons, New York, N.Y., (1st Edition, 1981) which can be added or removed using the procedures set forth therein. Examples of protected hydroxyl groups include, but are not limited to, silyl ethers such as those obtained by reaction of a hydroxyl group with a reagent such as, but not limited to, t-butyidimethyl-chlorosilane, trimethylchlorosilane, triisopropylchlorosilane, triethylchlorosilane; substituted methyl and ethyl ethers such as, but not limited to methoxymethyl ether, methythiomethyl ether, benzyloxymethyl ether, t-butoxymethyl ether, 2-methoxyethoxymethyl ether, tetrahydropyranyl ethers, 1-ethoxyethyl ether, allyl ether, benzyl ether; esters such as, but not limited to, benzoylformate, formate, acetate, trichloroacetate, and trifluoroacetate. Examples of protected amine groups include, but are not limited to, amides such as, formamide, acetamide, trifluoroacetamide, and benzamide; imides, such as phthalimide, and dithiosuccinimide; and others. Examples of protected sulfhydryl groups include, but are not limited to, thioethers such as S-benzyl thioether, and S-4-picolyl thioether; substituted S-methyl derivatives such as hemithio, dithio and aminothio acetals; and others.

FIG. 1 illustrates a general synthetic route for compounds containing the following core structure:

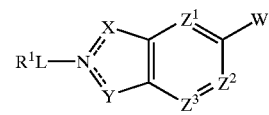

In the first part of the synthesis the non-guanidino linked portion of the bicyclic core is functionalized. In one embodiment of the method of the invention, the condensation of an amine and an anhydride gives an N-substituted phthalimide. Alternatively, if a phthalimide is used as the starting material, the phthalimide nitrogen may be functionalized by displacement of an activated alcohol. These transformations allow access to a wide range of N-substituted intermediates by varying the type of $R_1OH$ or $R_1NH_2$ inputs. It can further be appreciated that use of the appropriate starting materials for the bicyclic core can also provide, for example, compounds of the invention containing a nitrogen atom in the aromatic ring to which the guanidino moiety is attached.

In the next phase of the synthetic route, the functionalized imide may be reduced to the lactam via a two step process. After separation of the desired lactam regioisomer, the primary amine may be activated by treatment with thiophosgene to form the thioisocyanate. Sequential coupling of two amines yields the desired lactam products, which can exist in two tautomeric forms. One skilled in the art would recognize that alternative couplings of amines to thioureas exist, such as the use of a myriad of carbodiimide based coupling reagents or alkylation of the sulfur atom with an alkyl halide prior to addition of an amine.

FIG. 1

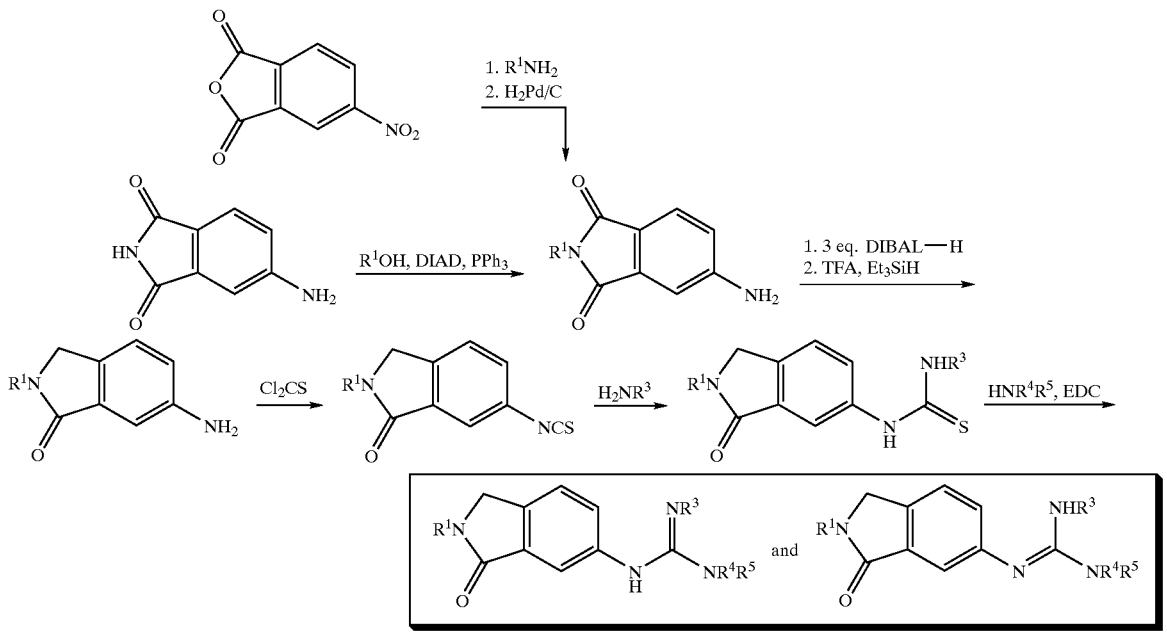

Use of the other regioisomer obtained from the reduction step would lead to the regioisomeric lactam and its tautomer shown in FIG. 2 below.

FIG. 2

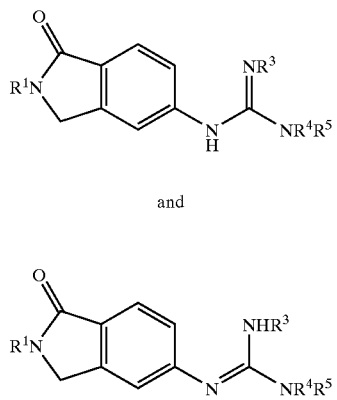

Furthermore, the reduction steps in FIG. 1 can be omitted in its entirety and the reaction scheme can be carried through to give the guanidino imide and its tautomer shown in FIG. 3 as products. Conversely, both carbonyl groups can be fully reduced to give the tetrahydro analogs.

FIG. 3

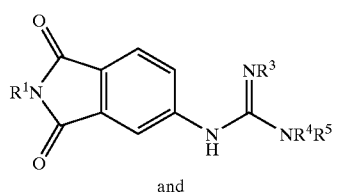

-continued

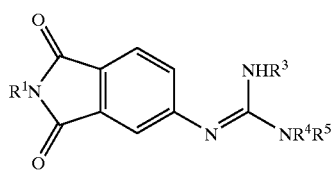

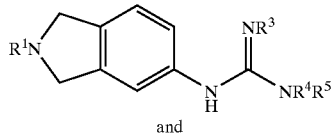

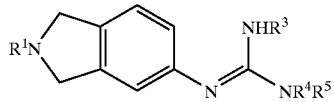

Additional structural variations within the non-guanidino linked portion of the bicyclic core itself can be achieved by starting with, for example, bicyclic lactams or bicyclic cyloamido compounds. These scaffolds can be generally be functionalized by methods known in the art such as N-alkylation with a variety of electrophiles (see R. Larock, *Comprehensive Organic Transformations;* VHC Publisher's Inc., 1989). Bicyclic lactams can also be generally functionalized as shown in FIG. 4. An amine or its activated equivalent (for example an alkyl aluminum amide) is first coupled with a lactone. The resulting product is then used in a subsequent cyclodehydration reaction (for example a Mitsunobu reaction) to give the functionalized bicyclic core. The guanidino moiety may then be installed as described above.

FIG. 4

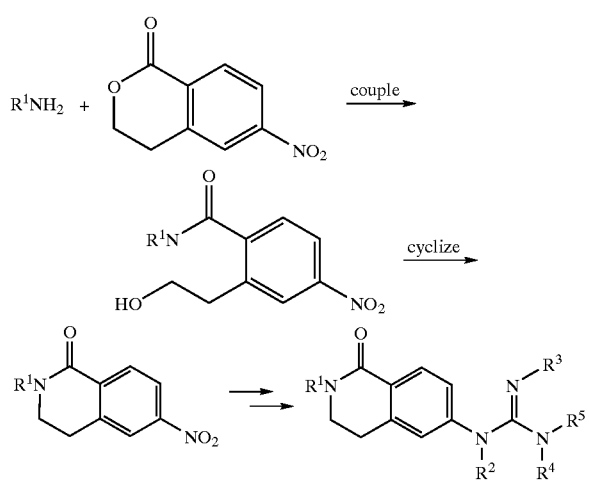

FIG. 5 illustrates a general synthetic route for compounds of the invention containing the benzimidazole core structure. An activated acid is first condensed with a diaminonitrophenyl starting material followed by exposure of the resulting product to acidic conditions to provide the benzimidazole core. The nitro moiety is then reduced and converted to the functionalized quanidino substituent as described above.

FIG. 5

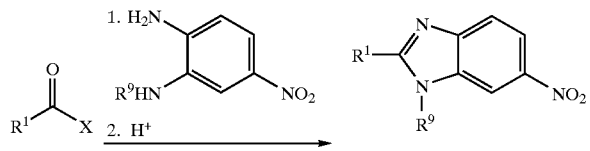

In another embodiment of the invention, benzoxazole and benzthiazole comprise the bicyclic core. These compounds may be constructed as shown in FIG. 6. Commercially available (Aldrich) 6-nitrobenzothiazole may be treated with base and quenched with N-chlorosuccinimide to give the halogenated intermediate. This compound may then be used in a number of metal mediated coupling reactions (for example Heck, Stille, Sonogashira coupling reactions) to functionalize the bicyclic core. The nitro group then serves as the attachment point for the guanidino unit.

FIG. 6

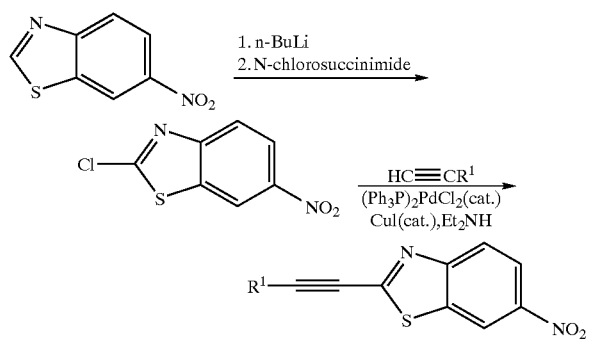

The present invention, thus generally described, will be understood more readily by reference to the following examples, which are provided by way of illustration and are not intended to be limiting of the present invention.

EXAMPLES

Compounds were named using the ACD/Name v. 4.53.

The following abbreviations are used throughout the Examples:

| | |
|---|---|
| eq | equivalent |
| DIAD | diisopropylazodicarboxylate |
| DIBAL—H | diisobutlyaluminum hydride |
| EDC | 1-ethyl-3-(3'-dimethylaminopropyl)-carbodiimide hydrochloride |
| EtOAc | ethylacetate |
| THF | tetrahydrofuran |
| TFA | trifluoroacetic acid |

Analytical Methodology

HPLC System: HPLC was run on a Waters 2690 HPLC system.
column=Reliasil 50×4.6 mm (5 μm pore size)
method: (note: all solvents include 0.1% TFA)

| time (minutes) | flow rate (mL/min) | % water | % CAN |
|---|---|---|---|
| init. | 2 | 95 | 5 |
| 15 | 2 | 20 | 80 |
| 15.5 | 2 | 0 | 100 |
| 17.5 | 2 | 0 | 100 |
| 18.5 | 2 | 95 | 5 |

Model HPLC=(Water 2690 Separations Module)
detector=(Water 996 photodiode array detector)
LCMS were run on HP Series 1100 LCMS system
HP LCMS (1100 series)
HP MSD (1100 series)

| time (minutes) | flow rate (mL/min) | % A* | % B* |
|---|---|---|---|
| 0 | 0.8 | 95 | 5 |
| .2 | 0.8 | 95 | 5 |
| 3.7 | 0.8 | 5 | 95 |
| 3.85 | 0.8 | 95 | 5 |
| 5 | 0.8 | 95 | 5 |

*solvent A = (water + 0.05% TFA) and solvent B = (Acetonitrile + 0.05% TFA)

column temp=30° C.
column=(brand =Eclipse XDB) 50×2 mm (5 μ) (C18)
MS Methodology
MWT: 150–800
CV: 20
Ionization: ESP+
  i. Data: Centroid
Repeat: 1
Scan Time: 2 seconds

EXAMPLE 1

Preparation of (3S)-N-{2-[2-(2,4-dichlorophenyl)ethyl]-1-oxo-2,3-dihydro-1H-isoindol-5-yl}-3-methyl-N'-[(1S,2S,3S,5R)-2,6,6-trimethylbicyclo[3.1.1]hept-3-yl]piperazine-1-carboximidamide Step 1. Preparation of 2-[2-(2,4-dichlorophenyl)ethyl]-5-nitro-1H-isoindole-1,3(2H)-dione 2-(2,4-dichlorophenyl)ethanamine was suspended in toluene with 4-nitrophthalic anhydride (1 eq) and heated to 150°

C. After 2 hours, the reaction was cooled and checked for completion by LC/MS. The solvent was then removed in vacuo and the resulting product was taken on to the next step without further purification. $R_t$ 3.36 minutes (HP LCMS), LC/MS m/z 365.1 (MH+).

Step 2 Preparation of 5-amino-2-[2-(2,4-dichlorophenyl)ethyl]-1H-isoindole-1,3(2H-dione The product of the previous step was taken up in ethanol (or methanol) and purged with dry nitrogen. To this solution was introduced activated Pd/C (10% w/w, 0.1 eq) and the mixture was hydrogenated for about 30 minutes or until complete by LC/MS. The mixture was then filtered through celite, concentrated in vacuo, and taken on to the next step. $R_t$ 2.95 minutes (HP LCMS), LC/MS m/z 335.0 (MH+).

Step 3 Preparation of 5-amino-2-[2-(2,4-dichlorophenyl)ethyl]-3-hydroxyisoindolin-1-one To a $CH_2Cl_2$ solution of the phthalimide was added dropwise DIBAL-H (3 eq, 1.0 M solution in $CH_2Cl_2$) at room temperature with good stirring. After stirring for one hour, the reaction was diluted with ether, NaF (12 eq), and distilled water (9 eq) and stirred for an additional hour. The reaction mixture was then filtered through celite to remove the aluminum precipitants. After washing the celite with additional $CH_2Cl_2$, the filtrate was then concentrated in vacuo to give a crude product (mixture of regioisomers) was then used in the following step without further purification. $R_t$ 2.09 minutes (HP LCMS) and 2.23 minutes (HP LCMS), LC/MS m/z 337.2 (MH+).

Step 4 Preparation of 5-amino-2-[2-(2,4-dichlorophenyl)ethyl]isoindolin-1-one

To a $CH_2Cl_2$ (0.1 M solution) of the crude product from the previous step was added dropwise triflouroacetic acid (6.0 eq) followed immediately by dropwise addition of triethylsilane (2.9 eq). After stirring for an additional 15 minutes, the mixture was concentrated in vacuo. The crude product of two regioisomeric lactams was then dissolved in acetonitrile and purified via reverse phase (C18) prep HPLC. The fractions for the desired regioisomeric lactam product (later retention time) were collected, frozen, and lyophilized. $R_t$ 7.24 minutes, LC/MS m/z 321.1 (MH+).

Step 5 Preparation of 2-[2-(2,4-dichlorophenyl)ethyl]-5-isothiocyanato-isoindolin-1-one To a 0.5 M solution of the amine in acetone (0° C. ice bath) was added thiophosgene (3 eq) dropwise. After 30 minutes, the reaction mixture was allowed to warm to room temperature. After two hours, the reaction mixture was concentrated in vacuo to remove solvent and excess thiophosgene. The crude isothiocyanate product was then used in the next step without further purification. $R_t$ 3.43 minutes (HP LCMS), LC/MS m/z 363.1 (MH+).

Step 6 Preparation of N-{2-[2-(2,4-dichlorophenyl)ethyl]-1-oxo-2,3-dihydro-1H-isoindol-5-yl}-N'-[(1S,2S,3S,5R)-2,6,6-trimethylbicyclo[3.1.1]hept-3-yl]thiourea To a solution of the crude isothiocyanate in dry acetonitrile (0.5 M solution) was added (+)-isopinocampheyl amine (1.5 eq). After stirring overnight, the reaction mixture was concentrated in vacuo and the thiourea product was dissolved in $CH_2Cl_2$ and purified via flash chromatography (1:1 Hexanes:EtOAc). Fractions containing the thiourea product were concentrated in vacuo and dried to yield a creamish white colored solid. $R_t$ 14.53 minutes, LC/MS m/z 516.4 (MH+).

Step 7 Preparation of (3S)-N-{2-[2-(2,4-dichlorophenyl)ethyl]-1-oxo-2,3-dihydro-1H-isoindol-5-yl}-3-methyl-N'-[(1S,2S,3S,5R)-2,6,6-trimethylbicyclo[3.1.1]hept-3-yl]piperazine-1-carboximidamide To a solution of the thiourea in THF (dry, 0.5 M) in a dry vial was added (S)-(+)-2-methylpiperazine (3 eq) and EDC (3 eq). The vial was capped tightly and heated to 80° C. for approximately 2 hours. The mixture was then allowed to cool to room temperature and concentrated in vacuo. The reaction mixture was dissolved in DMSO along with TFA (1 eq) and purified by prep HPLC. The pure fractions were collected, frozen, and dried via lyopholization to give the product as a white solid. $R_t$ 8.36 minutes, LC/MS m/z 582.5 (MH+).

EXAMPLE 2

Preparation of (3S)-N-{2-[2-(2,4-dichlorophenyl)ethyl]-1,3-dioxo-2,3-dihydro-1H-isoindol-5-yl}-3-methyl-N'-[(1S,2S,3S,5R)-2,6,6-trimethylbicyclo[3.1.1]hept-3-yl]piperazine-1-carboximidamide Step 1 Preparation of 2-[2-(2,4-dichlorophenyl)ethyl]-5-nitro-1H-isoindole-1,3(2H-dione 2-(2,4-dichlorophenyl)ethanamine was suspended in toluene with 4-nitrophthalic anhydride (1 eq) and heated to 150° C. After 2 hours, the reaction was cooled and checked for completion by LC/MS. The solvent was then removed in vacuo and the resulting product was taken on to the next step without further purification. $R_t$ 3.91 minutes, LC/MS m/z 365.1 (MH+).

Step 2 Preparation of 5-amino-2-[2-(2,4-dichlorophenyl)ethyl]-1H-isoindole-1,3(2H)-dione The product of the previous step was taken up in ethanol (or methanol) and purged with dry nitrogen. To this solution was introduced activated Pd/C (10% w/w, 0.1 eq) and the mixture was hydrogenated for about 30 minutes or until complete by LC/MS. The mixture was then filtered through celite, concentrated in vacuo, and taken on to the next step. $R_t$ 2.96 minutes (HP LCMS), LC/MS m/z 335.1 (MH+).

Step 3 Preparation of 2-[2-(2,4-dichlorophenyl)ethyl]-5-isothiocyanatoiso-1H-isoindole-1,3(2H)dione To a 0.5 M solution of the amine in acetone (0° C. ice bath) was added thiophosgene (3 eq) dropwise. After 30 minutes, the reaction mixture was allowed to warm to room temperature. After two hours, the reaction mixture was concentrated in vacuo to remove solvent and excess thiophosgene. The crude isothiocyanate product was then used in the next step without further purification. $R_t$ 3.75 minutes (HP LCMS), LC/MS m/z 377.0 (MH+).

Step 4 Preparation of N-{2-[2-(2,4-dichlorophenyl)ethyl]-1,3-dioxo-2,3-dihydro-1H-isoindol-5-yl}-N'-[(1S,2S,3S,5R)-2,6,6-trimethylbicyclo[3.1.1]hept-3-yl]thiourea To a solution of the crude isothiocyanate in dry acetonitrile (0.5 M solution) was added (+)-isopinocampheyl amine (1.5 eq). After stirring overnight, the reaction mixture was concentrated in vacuo and the thiourea product was dissolved in $CH_2Cl_2$ and purified via flash chromatography (1:1 Hexanes:EtOAc). Fractions containing the thiourea product were concentrated in vacuo and dried overnight via lyophilization to yield a yellowish-brown solid. $R_t$ 3.98 minutes (HP LCMS), LC/MS m/z 596.1 (MH+).

Step 5 Preparation of (3S)-N-{2-[2-(2,4-dichlorophenyl)ethyl]-1-oxo-2,3-dihydro-1H-isoindol-5-yl}-3-methyl-N'-[(1S,2S,3S,5R)-2,6,6-trimethylbicyclo[3.1.1]hept-3-yl]piperazine-1-carboximidamide To a solution of the thiourea in THF (dry, 0.5 M) in a dry vial was added (S)-(+)-2-methylpiperazine (3 eq) and EDC (3 eq). The vial was capped tightly and heated to 80° C. for approximately 2 hours. The mixture was then allowed to cool to room temperature and concentrated in vacuo. The reaction mixture was dissolved in DMSO along with TFA (1 eq) and purified by prep HPLC. The pure fractions were collected, frozen, and dried via lyopholization to give the product as a white solid. $R_t$ 9.57 minutes, LC/MS m/z 596.3 (MH+).

Examples 3–16 were prepared using the procedures described for 1 and 2.

EXAMPLE 3

(3S)-N{2-[2-(2,4-dichlorophenyl)ethyl]-3-oxo-2,3-dihydro-1H-isoindol-5-yl}-3-methyl-N'-[(1S,2S,3S,5R)-2,6,6-trimethylbicyclo[3.1.1]hept-3-yl]piperazine-1-carboximidamide Synthesized from 2-(2,4-dichlorophenyl)ethanamine. $R_t$ 8.72 minutes, LC/MS m/z 582.5 (MH+).

EXAMPLE 4

(3S)-N-[2-(2,4-dichlorobenzyl)-1,3-dioxo-2,3-dihydro-1H-isoindol-5-yl]-3-methyl-N'-[(1S,2S,3S,5R)-2,6,6-trimethylbicyclo[3.1.1]hept-3-yl]piperazine-1-carboximidamide Synthesized from 1-(2,4-dichlorophenyl)methanamine. $R_t$ 8.72 minutes, LC/MS m/z 582.5 (MH+).

EXAMPLE 5

(3S)-N-{2-[(1S)-1-benzyl-2-hydroxyethyl]-1,3-dioxo-2,3-dihydro-1H-isoindol-5-yl}-3-methyl-N'-[(1S,2S,3S,5R)-2,6,6-trimethylbicyclo[3.1.1]hept-3-yl]piperazine-1-carboximidamide Synthesized from L-phenylalaninol. $R_t$ 7.56 minutes, LC/MS m/z 558.7 (MH+).

EXAMPLE 6

(3S)-N-{2-[(1R)-1-benzyl-2-hydroxyethyl]-1,3-dioxo-2,3-dihydro-1H-isoindol-5-yl}-3-methyl-N'-[(1S,2S,3S,5R)-2,6,6-trimethylbicyclo[3.1.1]hept-3-yl]piperazine-1-carboximidamide Synthesized from D-phenylalaninol. $R_t$ 7.52 minutes, LC/MS m/z 558.7 (MH+).

EXAMPLE 7

(3S)-N-{2-[2-(2-fluoro4-methylphenyl)ethyl]-1-oxo-2,3-dihydro-1H-isoindol-5-yl}-3-methyl-N'-[(1S,2S,3S,5R)-2,6,6-trimethylbicyclo[3.1.1]hept-3-yl]piperazine-1-carboximidamide Synthesized from 2-(3-fluoro-5-methylphenyl)ethanamine. $R_t$ 7.8 minutes, LC/MS m/z 546.2 (MH+).

EXAMPLE 8

(3S)-N-{2-[(1S)-1-(2,4-dichlorobenzyl)-2-hydroxyethyl]-1,3-dioxo-2,3-dihydro-1H-isoindol-5-yl}-3-methyl-N'-[(1S,2S,3S,5R)-2,6,6-trimethylbicyclo[3.1.1]hept-3-yl]piperazine-1-carboximidamide Synthesized from L-2,4-dichlorophenylalaninol, obtained in one step from the reduction of L-2,4-dichlorophenylalanine (see, for example, *JOC* 2000, 65, 5037–5042). $R_t$ 8.46 minutes, LC/MS m/z 626.2 (MH+).

EXAMPLE 9

(3S)-N-{2-[(1S)-1-(2,4-dichlorobenzyl)-2-hydroxyethyl]-1-oxo-2,3-dihydro-1H-isoindol-5-yl}-3-methyl-N'-[(1S,2S,3S,5R)-2,6,6-trimethylbicyclo[3.1.1]hept-3-yl]piperazine-1-carboximidamide Synthesized from L-2,4-dichlorophenylalaninol, obtained in one step from the reduction of L-2,4-dichlorophenylalanine (see, for example, *JOC* 2000, 65, 5037–5042). $R_t$ 7.71 minutes, LC/MS m/z 612.2 (MH+).

EXAMPLE 10

(3S)-N-{2-[2-(2-fluoro-4-methoxyphenyl)ethyl]-1,3-dioxo-2,3-dihydro-1H-isoindol-5-yl)}-3-methyl-N'-[(1S,2S,3S,5R)-2,6,6-trimethylbicyclo[3.1.1]hept-3-yl]piperazine-1-carboximidamide Synthesized from 2-(2-fluoro4-methoxyphenyl)ethanamine. $R_t$ 8.4 minutes, LC/MS m/z 576.2 (MH+).

EXAMPLE 11

(3S)-N-{2-[2-(2,4-difluorophenyl)ethyl]-1,3-dioxo-2,3-dihydro-1H-isoindol-5-yl}-3-methyl-N'-[(1S,2S,3S,5R)-2,6,6-trimethylbicyclo[3.1.1]hept-3-yl]piperazine-1-carboximidamide Synthesized from 2-(2,4-difluorophenyl)ethanamine. $R_t$ 8.53 minutes, LC/MS m/z 564.2 (MH+).

EXAMPLE 12

(3S)-N-{2-[2-(2,4-dimethoxyphenyl)ethyl]-1,3-dioxo-2,3-dihydro-1H-isoindol-5-yl}-3-methyl-N'-[(1S,2S,3S,5R)-2,6,6-trimethylbicyclo[3.1.1]hept-3-yl]piperazine-1-carboximidamide Synthesized from 2-(2,4-dimethoxyphenyl)ethanamine. $R_t$ 8.51 minutes, LC/MS m/z 588.3 (MH+).

EXAMPLE 13

(3S)-N-{2-[2-(2,4-dimethylphenyl)ethyl]-1,3-dioxo-2,3-dihydro-1H-isoindol-5-yl}-3-methyl-N'-[(1S,2S,3S,5R)-2,6,6-trimethylbicyclo[3.1.1]hept-3-yl]piperazine-1-carboximidamide Synthesized from 2-(2,4-dimethylphenyl)ethanamine. $R_t$ 9.43 minutes, LC/MS m/z 556.2 (MH+).

EXAMPLE 14

(3S)-N-{2-[(1S,2S)-2-hydroxy-1-(hydroxymethyl)-2-phenylethyl]-1,3-dioxo-2,3-dihydro-1H-isoindol-5-yl}-3-methyl-N'-[(1S,2S,3S,5R)-2,6,6-trimethylbicyclo[3.1.1]hept-3-yl]piperazine-1-carboximidamide Synthesized from (1S,2S)-(+)-2-amino-1-phenyl-1,3-propanediol. $R_t$ 6.68 minutes, LC/MS m/z 574.3 (MH+).

EXAMPLE 15

(3S)-N-{2-[(1R,2R)-2-hydroxy-1-(hydroxymethyl)-2-phenylethyl]-1,3-dioxo-2,3-dihydro-1H-isoindol-5-yl}-3-methyl-N'-[(1S,2S,3S,5R)-2,6,6-trimethylbicyclo[3.1.1]hept-3-yl]piperazine-1-carboximidamide Synthesized from (1R,2R)-(−)-2-amino-1-phenyl-1,3-propanediol. $R_t$ 6.64 minutes, LC/MS m/z 574.3 (MH+).

EXAMPLE 16

(3S)-N-{2-[(1S,2R)-2-hydroxy-1-(hydroxymethyl)-2-phenylethyl]-1,3dioxo-2,3-dihydro-1H-isoindol-5-yl}-3-methyl-N'-[(1S,2S,3S,5R)-2,6,6-trimethylbicyclo[3.1.1]hept-3-yl]piperazine-1-carboximidamide Synthesized from (1R,2S)-(+)-2-amino-1-phenyl-1,3-propanediol. $R_t$ 6.63 minutes, LC/MS m/z 574.3 (MH+).

EXAMPLE 17

(3S)-N-{2-[2-(2-fluoro-4-methoxyphenyl)ethyl]-1-oxo-2,3-dihydro-1H-isoindol-5-yl}-3-methyl-N'-[(1S,2S,3S,5R)-2,6,6-trimethylbicyclo[3.1.1]hept-3-yl]piperazine-1-carboximidamide Synthesized from 2-(2-fluoro-4-methoxyphenyl)ethanamine. $R_t$ 7.42 minutes, LC/MS m/z 562 (MH+).

EXAMPLE 18

(3S)-N-{2-[2-(2,4-difluorophenyl)ethyl]-1-oxo-2,3-dihydro-1H-isoindol-5yl}-3-methyl-N'-[(1S,2S,3S,5R)-2,6,6-trimethylbicyclo[3.1.1]hept-3-yl]piperazine-1-carboximidamide Synthesized from 2-(2,4-difluorophenyl)ethanamine. $R_t$ 7.5 minutes, LC/MS m/z 550 (MH+).

EXAMPLE 19

(3S)-N-{2-[2-(2,4-difluorophenyl)ethyl]-3-oxo-2,3-dihydro-1H-isoindol-5-yl}-3-methyl-N'-[(1S,2S,3S,5R)-2,6,6-trimethylbicyclo[3.1.1]hept-3-yl]piperazine-1-carboximidamide Synthesized from 2-(2,4-difluorophenyl)ethanamine. $R_t$ 7.82 minutes, LC/MS m/z 550 (MH+).

EXAMPLE 20

(3S)-N-{2-[2-(2,4-dimethylphenyl)ethyl]-1-oxo-2,3-dihydro-1H-isoindol-5-yl}-3-methyl-N'-[(1S,2S,3S,5R)-2,6,6-trimethylbicyclo[3.1.1]hept-3-yl]piperazine-1-carboximidamide Synthesized from 2-(2,4-dimethylphenyl)ethanamine. $R_t$ 8.21 minutes, LC/MS m/z 542.1 (MH+).

EXAMPLE 21

(3S)-N-{2-[2-(2,4-dimethylphenyl)ethyl]-3-oxo-2,3-dihydro-1H-isoindol-5-yl}-3-methyl-N'-[(1S,2S,3S,5R)-2,6,6-trimethylbicyclo[3.1.1]hept-3-yl]piperazine-1-carboximidamide Synthesized from 2-(2,4-dimethylphenyl)ethanamine. $R_t$ 8.5 minutes, LC/MS m/z 542.1 (MH+).

EXAMPLE 22

(3S)-N-{2-[2-(2,4-dichlorophenyl)ethyl]-1-oxo-1,2,3,4-tetrahydroisoquinolin-6-yl}-3-methyl-N'-[(1S,2S,5R)-2,6,6-trimethylbicyclo[3.1.1]hept-3-yl]piperazine-1-carboximidamide 6-nitroisochroman-1-one was treated with the dimethylaluminum amide prepared from 2-(2,4-dichlorophenyl)ethanamine, and the product obtained was cyclized using Mitsunobu conditions (as in Ian. Bell et al, Tetrahedron. Lett. (2000), 41, 1141–1145). The nitro group was then reduced, and the amine was converted to the substituted guanidine (as in steps 2–5 of Example 2 above) to give the title compound. $R_t$ 9.06 minutes, LC/MS m/z 596.1 (MH+).

EXAMPLE 23

(3S)-N-{2-[2-(2,4-dichlorophenyl)ethyl]-1H-benzimidazol-5-yl}-3-methyl-N'-[(1S,2S,3S,5R)-2,6,6-trimethylbicyclo[3.1.1]hept-3-yl]piperazine-1-carboximidamide 2,4-dichlorophenyl propionic acid (1.0 eq) was mixed with 4-nitro-1,2-phenylenediamine (1.1 eq) and EDC (1.5 eq) in THF at room temperature for 8 hours. The solution was diluted with ethyl acetate and washed with water (3×). The combined organic layers were dried over sodium sulfate, filtered, and concentrated in vacuo. The product was then subjected to refluxing glacial acetic acid for 30 minutes. After removal of the acetic acid in vacuo, the residue was free-based with sodium carbonate. The resulting compound was then subjected to the hydrogenation and guanidino functionalization conditions described in Example 2 above (steps 2, 3, 4, and 5) to give the desired product. $R_t$ 7.08 minutes, LC/MS m/z 567.2 (MH+).

Examples 24 and 25 can be prepared using the procedures described for Example 23.

EXAMPLE 24

(3S)-N{2-[2-(2,4-dimethylphenyl)ethyl]-1H-benzimidazol-6-yl}-3-methyl-N'-[(1S,2S,3S,5R)-2,6,6-trimethylbicyclo[3.1.1]hept-3-yl]piperazine-1-carboximidamide Synthesized from 3-(2,4-dimethylphenyl)propanoic acid. $R_t$ 6.93 minutes, LC/MS m/z 527.3 (MH+).

EXAMPLE 25

(3S)-N-{2-[2-(2-chloro-4-fluorophenyl)ethyl]-1H-benzimidazol-6-yI}-3-methyl-N'-[(1S,2S,3S,5R)-2,6,6-trimethylbicyclo[3.1.1]hept-3-yl]piperazine-1-carboximidamide Synthesized from 3-(2-chloro-4-fluorophenyl)propanoic acid. $R_t$ 6.54 minutes, LC/MS m/z 551.4 (MH+).

In addition to the synthesis described above, many of the synthetic transformations presented in U.S. Provisional Application No. 60/245,579 are relevant to the synthesis of the compounds of the present invention. Thus, U.S. Provisional Application No. 60/245,579, filed Nov. 6, 2000 is hereby incorporated by reference in its entirety.

In Vitro Data $EC_{50}$ values of test compounds were determined by treating cells expressing MC4-R with test compound and lysing the cells and measuring intercellular cAMP concentration with an Amersham-Pharmacia RPA-559 cAMP Scintillation Proximity Assay (SPA) kit. The following compounds were synthesized and tested according to this assay. The following compounds are merely illustrative and should not be construed as limiting of the instant invention. Compounds having an in vitro potency (as measured by $EC_{50}$ value) of less than 3 μM include:

(3S)-N-{2-[2-(2,4-dichlorophenyl)ethyl]-1-oxo-2,3-dihydro-1H-isoindol-5-yl}-3-methyl-N'-[(1S,2S,3S,5R)-2,6,6-trimethylbicyclo[3.1.1]hept-3-yl]piperazine-1-carboximidamide; (3S)-N-{2-[2-(2,4-dichlorophenyl)ethyl]-1-oxo-2,3-dihydro-1H-isoindol-5-yl}-3-methyl-N'-[(1S,2S,3S,5R)-2,6,6-trimethylbicyclo[3.1.1]hept-3-yl]piperazine-1-carboximidamide; (3S)-N-{2-[2-(2,4-dichlorophenyl)ethyl]-3-oxo-2,3-dihydro-1H-isoindol-5-yl}-3-methyl-N'-[(1S,2S,3S,5R)-2,6,6-trimethylbicyclo[3.1.1]hept-3-yl]piperazine-1-carboximidamide; (3S)-N-[2-(2,4-dichlorobenzyl)-1,3-dioxo-2,3-dihydro-1H-isoindol-5-yl]-3-methyl-N'-[(1S,2S,3S,5R)-2,6,6-trimethylbicyclo[3.1.1]hept-3-yl]piperazine-1-carboximidamide; (3S)-N-{2-[(1S)-1-benzyl-2-hydroxyethyl]-1,3-dioxo-2,3-dihydro-1H-isoindol-5-yl}-3-methyl-N'-[(1S,2S,3S,5R)-2,6,6-trimethylbicyclo[3.1.1]hept-3-yl]piperazine-1-carboximidamide; (3S)-N-{2-[(1R)-1-benzyl-2-hydroxyethyl]-1,3-dioxo-2,3-dihydro-1H-isoindol-5-yl}-3-methyl-N'-[(1S,2S,3S,5R)-2,6,6-trimethylbicyclo[3.1.1]hept-3-yl]piperazine-1-carboximidamide; (3S)-N-{2-[2-(2-fluoro-4-methylphenyl)ethyl]-1-oxo-2,3-dihydro-1H-isoindol-5-yl}-3-methyl-N'-[(1S,2S,3S,5R)-2,6,6-trimethylbicyclo[3.1.1]hept-3-yl]piperazine-1-carboximidamide; (3S)-N-{2-[(1S)-1-(2,4-dichlorobenzyl)-2-hydroxyethyl]-1,3-dioxo-2,3-dihydro-1H-isoindol-5-yl}-3-methyl-N'-[(1S,2S,3S,5R)-2,6,6-trimethylbicyclo[3.1.1]hept-3-yl]piperazine- 1-carboximidamide; (3S)-N-{2-[2-(2-fluoro4-methoxyphenyl)ethyl]-1,3-dioxo-2,3-dihydro-1H-isoindol-5-yl}-3-methyl-N'-[(1S,2S,3S,5R)-2,6,6-trimethylbicyclo[3.1.1]hept-3-yl]piperazine-1-carboximidamide; (3S)-N-{2-[2-(2,4-difluorophenyl)ethyl]-1,3-dioxo-2,3-dihydro-1H-isoindol-5-yl}-3-methyl-N'-[(1S,2S,3S,5R)-2,6,6-trimethylbicyclo[3.1.1]hept-3-yl]piperazine-1-carboximidamide; (3S)-N-{2-[2-(2,4-dimethoxyphenyl)ethyl]-1,3-dioxo-2,3-dihydro-1H-isoindol-5-yl}-3-methyl-N'-[(1S,2S,3S,5R)-2,6,6-trimethylbicyclo[3.1.1]hept-3-yl]piperazine-1-carboximidamide; (3S)-N-{2-[2-(2,4-dimethylphenyl)ethyl]-1,3-dioxo-2,3-dihydro-1H-isoindol-5-yl}-3-methyl-N'-[(1S,2S,3S,5R)-2,6,6-trimethylbicyclo[3.1.1]hept-3-yl]piperazine-1-carboximidamide; (3S)-N-{2-[(1S,2S)-2-hydroxy-1-(hydroxymethyl)-2-phenylethyl]-1,3-dioxo-2,3-dihydro-1H-isoindol-5-yl}-3-methyl-N'-[(1S,2S,3S,5R)-2,6,6-trimethylbicyclo[3.1.1]hept-3-yl]piperazine-1-carboximidamide; (3S)-N-{2-[(1R,2R)-2-hydroxy-1-(hydroxymethyl)-2-phenylethyl]-1,3-dioxo-2,3-dihydro-1H-isoindol-5-yl}-3-methyl-N'-[(1S,2S,3S,5R)-2,6,6-trimethylbicyclo[3.1.1]hept-3-yl]piperazine-1-carboximidamide; (3S)-N-{2-[(1S,2R)-2-hydroxy-1-(hydroxymethyl)-2-phenylethyl]-1,3-dioxo-2,3-dihydro-1H-isoindol-5-yl}-3-methyl-N'-[(1S,2S,3S,5R)-2,6,6-trimethylbicyclo[3.1.1]hept-3-yl]piperazine-1-carboximidamide; (3S)-N-{2-[2-(2-fluoro-4-methoxyphenyl)ethyl]-1-oxo-2,3-dihydro-1H-isoindol-5-yl}-3-methyl-N'-[(1S,2S,3S,5R)-2,6,6-trimethylbicyclo[3.1.1]hept-3-yl]piperazine-1-carboximidamide; (3S)-N-{2-[2-(2,4-difluorophenyl)ethyl]-1-oxo-2,3-dihydro-1H-isoindol-5-yl}-3-methyl-N'-[(1S,2S,3S,5R)-2,6,6-trimethylbicyclo[3.1.1]hept-3-yl]piperazine-1-carboximidamide; (3S)-N-{2-[2-(2,4-difluorophenyl)ethyl]-3-oxo-2,3-dihydro-1H-isoindol-5-yl}-3-methyl-N'-[(1S,2S,3S,5R)-2,6,6-trimethylbicyclo[3.1.1]hept-3-yl]piperazine-1-carboximidamide; (3S)-N-{2-[2-(2,4-dimethylphenyl)ethyl]-1-oxo-2,3-dihydro-1H-isoindol-5-yl}-3-methyl-N'-[(1S,2S,3S,5R)-2,6,6-trimethylbicyclo[3.1.1]hept-3-yl]piperazine-1-carboximidamide; (3S)-N-{2-[2-(2,4-dimethylphenyl)ethyl]-3-oxo-2,3-dihydro-1H-isoindol-5-yl}-3-methyl-N'-[(1S,2S,3S,5R)-2,6,6-trimethylbicyclo[3.1.1]hept-3-yl]piperazine-1-carboximidamide; (3S)-N{2-[2-(2,4-dichlorophenyl)ethyl]-1H-benzimidazol-5-yl}-3-methyl-N'-[(1S,2S,3S,5R)-2,6,6-trimethylbicyclo[3.1.1]hept-3-yl]piperazine-1-carboximidamide; (3S)-N-{2-[2-(2,4-dimethylphenyl)ethyl]-1H-benzimidazol-6-yl}-3-methyl-N'-[(1S,2S,3S,5R)-2,6,6-trimethylbicyclo[3.1.1]hept-3-yl]piperazine-1-carboximidamide; (3S)-N-{2-[2-(2,4-dichlorophenyl)ethyl]-1-oxo-1,2,3,4-tetrahydroisoquinolin-6-yl}-3-methyl-N'-[(1S,2S,5R)-2,6,6-trimethylbicyclo[3.1.1]hept-3-yl]piperazine-1-carboximidamide; (3S)-N-{2-[(1S)-1-(2,4-dichlorobenzyl)-2-hydroxyethyl]-1-oxo-2,3-dihydro-1H-isoindol-5-yl}-3-methyl-N'-[(1S,2S,3S,5R)-2,6,6-trimethylbicyclo[3.1.1]hept-3-yl]-1-piperazinecarboximidamide; and (3S)-N-{2-[2-(2-chloro-4-fluorophenyl)ethyl]-1H-benzimidazol-6-yl}-3-methyl-N'-[(1S,2S,3S,5R)-2,6,6-trimethylbicyclo[3.1.1]hept-3-yl]piperazine-1-carboximidamide.

In Vivo Studies of MC4-R Agonists on Energy Intake, Body Weight, Hyperinsulinemia, and Glucose Levels In vivo studies are conducted to observe the effect of MCR-4 agonists on energy intake, body weight, hyperinsulinemia, and glucose levels. All studies are conducted with male 9–10 week old ob/ob mice which display early onset of obesity, insulin resistance and diabetes due to leptin deficiency. Mice are acclimated in the facility for 1 week before studies and are caged individually. Vehicle-treated (control) and drug treated mice studies are always run in parallel. In multi-day studies, mice (8–15 per group) are monitored for baseline body weight, fasting levels of glucose, insulin, blood lipids and energy expenditure and then are injected twice daily (9 a.m. and 5 p.m.) with 3 mg/kg of an MC4-R agonist according to the invention for 2–4 weeks. Body weight as well as food and water intake are monitored daily. Animals are fasted overnight for measurements of fasting levels of glucose, insulin, and lipids once a week until the end of the study. Energy expenditure (resting metabolic rate, i.e., $O_2$ consumption and $CO_2$ production) are monitored in air tight chambers at the end of the study on fed animals. $O_2$ consumption and $CO_2$ production are measured using Oxymax systems (Columbus Instruments). Oral glucose tolerance test (OGTT—a routine test for diabetes and glucose intolerance) is performed on overnight fasted mice at the end of the study. Blood glucose and oral glucose tolerance are measured using a glucose monitor (Onetouch sold by Lifescan). Free fatty acids are measured using an nonesterfifed free fatty acids enzymatic assay (Waco Chemicals). Serum Insulin levels are measured by immunoassay (Alpco).

The results of the above studies show that a significant reduction in food intake occurs in those mice treated IP with the compounds of the present invention. The results also show that mice treated with the compounds of the present invention show a significant body weight reduction compared to mice not treated with the compounds of the present invention. Vehicle treated mice show an increase in blood glucose consistent with the rapid progression of diabetes in this mouse strain, whereas the onset of diabetes is slowed down in mice treated with the compounds of the present invention. Oral glucose tolerance tests are performed. Orally administered glucose quickly elevates blood glucose similar to after eating a meal. Vehicle treated mice show an elevated response to glucose consistent with their diabetic state, whereas mice treated with the compounds of the present invention show a very much improved glucose disposal. Mice are fasted overnight and free fatty acid levels are measured the following morning. Vehicle treated mice show elevated free fatty acid levels consistent with their obese state, whereas mice treated with the compounds of the present invention show a dramatic 50% decrease. Serum insulin levels are measured one hour after single IP dosing of compounds of the present invention in overnight fasted ob/ob mice. Mice treated with the compounds of the present invention show a dose dependent decrease relative to vehicle.

What is claimed is:

1. A compound of formula I

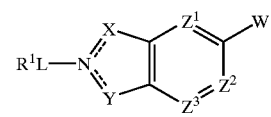

wherein

X and Y are independently selected from the group consisting of $CH_2$, C=O, and C=S;

43

W is selected from the group consisting of

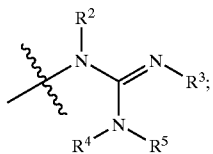

L is selected from the group consisting of O, C(O), OC(O), and a covalent bond;

$Z^1$, $Z^2$, and $Z^3$ are $CR^8$;

$R^1$ is selected from the group consisting of H, and substituted and unsubstituted arylalkyl, aryl, cycloalkyl, cycloalkylalkyl, alkenyl, alkynyl, and alkyl groups;

$R^2$ is selected from the group consisting of H, and substituted and unsubstituted alkyl, alkenyl, elkynyl, cycloalkylalkyl, aryl, and arylalkyl groups;

$R^3$ is selected from the group consisting of H, and substituted and unsubstituted alkyl, alkenyl, alkynyl, cycloalkyl, arylalkyl, and cycloalkylalkyl groups, or $R^2$ and $R^3$ may join together to form a ring containing at least two N atoms;

$R^4$ is selected from the group consisting of H, and substituted and unsubstituted alkyl, alkenyl, alkynyl, cycloalkyl, aryl, heteroaryl, heterocyclyl, arylalkyl, heteroarylalkyl, and cycloalkylalkyl groups, or R and R' may join together to form a ring containing at least two N atoms;

$R^5$ is selected from the group consisting of H, and substituted and unsubstituted alkyl, alkenyl, alkynyl, cycloalkyl, aryl, heteroaryl, heterocyclyl, arylalkyl, heteroarylalkyl, and cycloalkylalkyl groups, or $R^4$ and $R^5$, together with the nitrogen to which they are bound, form a substituted or unsubstituted heterocyclyl or heteroaryl group, or $R^3$ and $R^5$ may join together to form a ring containing at least two N atoms;

$R^8$ is selected from the group consisting of H, Cl, I, F, Br, OH, $NH_2$, CN, $NO_2$, and substituted and unsubstituted alkoxy, amino, alkyl, alkenyl, alkynyl, alkylamino, dialkylamino, cycloalkyl, aminocarbonyl, alkyisminocarbonyl, dialkylaminocarbonyl, cycloalkylaminocarbonyl, and arylaminocarbonyl groups; and $R^9$ prodrugs thereof, pharmaceutically acceptable salts thereof, stereolsomers thereof, tautomers thereof, hydrates thereof, hydrides thereof, or solvates thereof.

2. A composition comprising the compound according to claim 1 and a pharmaceutically acceptable carrier.

3. A method of treating an MC4-R mediated disease, comprising administering to a subject in need thereof, the compound according to claim 1, wherein the MC4-R mediated disease is obesity.

4. A method of treating an MC4-R mediated disease, comprising administering to a subiect in need thereof, the comnound according to claim 1, wherein the disease is type II diabetes.

5. The compound of claim 1, wherein X is $CH_2$ and Y is C=O.

6. The compound of claim 1, wherein X is C=O and Y is $CH_2$.

7. The compound of claim 1, wherein X is C=O and Y is C=O.

8. The compound of claim 1, wherein L is a covalent bond.

44

9. The compound of claim 1, wherein $Z^1$, $Z^2$, and $Z^3$ are all CH.

10. The compound of claim 1, wherein $R^1$ is a substituted or unsubstituted arylalkyl group.

11. The compound of claim 1, wherein $R^1$ is a 2,4-disubstituted phenethyl group.

12. The compound of claim 1, wherein $R^2$ is H.

13. The compound of claim 1, wherein $R^4$ and $R^5$, together with the nitrogen to which they are bound, form a substituted or unsubstituted heterocyclyl group.

14. The compound of claim 1, wherein $R^4$ and $R^5$, together with the nitrogen to which they are bound, form a substituted or unsubstituted piperazino, morpholino, pyrrolidino, piperidino, homopiperazino, or azepino group.

15. The compound of claIm 1, wherein $R^4$ and $R^5$, together with the nitrogen to which they are bound, form a substituted or unsubstituted piperazino group.

16. The compound of claim 1, wherein $R^4$ and $R^5$, together with the nitrogen to which they are bound, form a piperazino group substituted with one or two methyl groups.

17. The compound of claim 1, wherein $R^3$ is selected from substituted or unsubstituted cycloalkyl, alkenyl, alkyl, or aryl groups.

18. The compound of claim 1, wherein $R^3$ is selected from substituted or unsubstituted cyclohexyl, 2-alkylcyclohexyl, 2,2-dialkylcyclohexyl, 2,3-dialkylcyclohexyl, 2,4-dialkylcyclohexyl, 2,5-dialkylcyclohexy, 2,6-dialkylcyclohexyl, 3,4-dialkylcyclohexyl, 3-alkylcyclohexyl, 4-alkylcyclohexyl, 3,3,5-trialkylcyclohexyl, cyclohexylmethyl, 2-aminocyclohexyl, 3-aminocyclohexyl, 4-aminocyclohexyl, 2,3-diaminocyclohexyl, 2,4-diaminocyclohexyl, 3,4-diaminocyclohexyl, 2,5-diaminocyclohexyl, 2,6-diaminocyclohexyl, 2,2-diaminocyclohexyl, 2-alkoxycyclohexyl, 3-alkoxycyclohexyl, 4-alkoxycyclohexyl, 2,3-dialkoxycyclohexyl, 2,4-dialkoxycyclohexyl, 3,4-dialkoxycyclohexyl, 2,5-dialkoxycyclohexyl 2,6-dialkoxycyclohexyl, 2,2-dialkoxycyclohexyl, 2-alkylthiocyclohexyl, 3-alkylthiocyclohexyl. 4-alkyithiocyclohexyl, 2,3-dialkylthiocyclohexyl, 2,4-dialkylthiocyclohexyl, 3,4-dialkylthiocyclohexyl, 2,5-dialkylthlocyclohexyl, 2,6-dialkylthiocyclohexyl, 2,2-dialkylthiocyclohexyl, cyclopentyl, cycloheptyl, cyclohexenyl, isopropyl, n-butyl, cyclooctyl, 2-arylcyclohexyl, 2-phenylcyclohexyl, 2-arylalkylcyclohexyl, 2-benzylcyclohexyl, 4-phenylcyclohexyl, adamantyl, isocamphenyl, carenyl, 7,7-dialkylnorbornyl, bornyl, norbornyl, or decalinyl groups.

19. The compound of claim 1, wherein $R^3$ is selected from substituted or unsubstituted cyclohexyl, 2-methylcyclohexyl, 2,2-dimethylcyclohexyl, 2,3-dimethylcyclohexyl, 2,4-dimethylcyclohexyl, 2,5-dimethylcyclohexyl, 2,6-dimethylcyclohexyl, 3,4-dimethylcyclohexyl, 3-methylcyclohexyl, 4-methylcyclohexyl, cyclohex-3-enyl, 3,3,5-trimethylcyclohexyl, 4-t-butylcyclohexyl, 2-methylcycloheptyl, cyclohexylmethyl, isopinocampheyl, 7,7-dimethylnorbomyl, 4-isopropylcyclohexyl, 2,6,6-trimethylbicyclo[3.1.1]heptyl, or 3-methylcycloheptyl groups.

20. The compound of claim 1, wherein $R^5$ is selected from substituted or unsubstituted aikyl, arylalkyl, or heteroarylalkyl groups.

* * * * *

UNITED STATES PATENT AND TRADEMARK OFFICE
CERTIFICATE OF CORRECTION

PATENT NO. : 6,716,840 B2
DATED : April 6, 2004
INVENTOR(S) : Chu et al.

It is certified that error appears in the above-identified patent and that said Letters Patent is hereby corrected as shown below:

<u>Title page</u>,
Item [74], *Attorney, Agent, or Firm*, delete the name "Robert P. Blackbur" and replace with -- Robert P. Blackburn --.

<u>Column 2</u>,
Line 13, delete the phrase "There is a need to for potent" and replace it with -- There is a need for potent --.
Line 36, delete the semi-colon at the end of the phrase "$C(=O)-(CR^6R^7)_n;$" and replace it with a comma to read -- $C(=O)-(CR^6R^7)_n,$ -- .

<u>Column 4</u>,
Line 60, delete "7,7-dimethyinorbornyl" and replace it with -- 7,7-dimethylnorbornyl --.

<u>Column 27</u>,
Lines 23-24, delete the words "binders, a thickeners, buffers, a sweeteners, " and replace them with -- binders, thickeners, buffers, sweeteners, --.

<u>Column 29</u>,
Line 58, delete the word "farhiliar" and replace it with -- familiar --.

<u>Column 30</u>,
Line 18, delete "t-butyidimethyl-chlorosilane" and replace it with -- t-butyldimethyl-chlorosilane --.

<u>Column 32</u>,
Line 55, delete the phrase "These scaffolds can be generally be" and replace it with -- These scaffolds can generally be --.

<u>Column 37</u>,
Line 1, of Example 7, insert a hyphen between "fluoro" and "4" to read -- (2-fluoro-4-methylphenyl) --.

<u>Column 41</u>,
Lines 1 and 2, insert a hyphen between "fluoro" and "4" to read -- 2-fluoro-4-methoxyphenyl) --.

<u>Column 42</u>,
Line 24, delete the word "nonesterfifed" and replace it with -- nonesterified --.

UNITED STATES PATENT AND TRADEMARK OFFICE
CERTIFICATE OF CORRECTION

PATENT NO. : 6,716,840 B2
DATED : April 6, 2004
INVENTOR(S) : Chu et al.

It is certified that error appears in the above-identified patent and that said Letters Patent is hereby corrected as shown below:

Column 43,
Line 18, delete "elkynyl" and replace it with -- alkynyl --.
Line 28-29, delete "R and R" and replace it with -- $R^2$ and $R^4$ --.
Line 43, delete "alkyisminocarbonyl," and replace it with -- alkylaminocarbonyl, --.
Line 45, delete "$R^9$" after the word "and".
Line 47, delete "stereolsomers" and replace it with -- stereoisomers --.

Column 44,
Line 16, delete the word "claIm" and replace it with -- claim --.
Line 28, delete the word "2,5-dialkylcyclohexy," and replace it with
-- 2,5-dialkylcyclohexyl, --.
Line 41, delete the word "4-alkyithiocyclohexyl," and replace it with
-- 4-alkylthiocyclohexyl, --.
Line 43, delete the word "2,5-dialkylthlocyclohexyl," and replace it with
-- 2,5-dialkylthiocyclohexyl, --.

Signed and Sealed this

Seventh Day of June, 2005

JON W. DUDAS
*Director of the United States Patent and Trademark Office*